United States Patent
Wynn et al.

(10) Patent No.: US 7,282,206 B2
(45) Date of Patent: Oct. 16, 2007

(54) TREATMENT OF FIBROSIS BY ANTAGONISM OF IL-13 AND IL-13 RECEPTOR CHAINS

(75) Inventors: Thomas A. Wynn, Silver Spring, MD (US); Monica G. Chiaramonte, Rockville, MD (US); Mary Collins, Natick, MA (US); Debra Donaldson, Medford, MA (US); Lori Fitz, Arlington, MA (US); Tamlyn Neben, Walnut Creek, CA (US); Matthew J. Whitters, Hudson, MA (US); Clive Wood, Boston, MA (US)

(73) Assignees: Wyeth, Madison, NJ (US); The United States of America as represented by the Department of Health and Human Services, Washington, DC (US)

( * ) Notice: Subject to any disclaimer, the term of this patent is extended or adjusted under 35 U.S.C. 154(b) by 470 days.

(21) Appl. No.: 10/671,034

(22) Filed: Sep. 25, 2003

(65) Prior Publication Data

US 2005/0096268 A1 May 5, 2005

Related U.S. Application Data

(62) Division of application No. 09/301,808, filed on Nov. 29, 1999, now Pat. No. 6,664,227.

(51) Int. Cl.
*A61K 39/395* (2006.01)
*A61K 39/00* (2006.01)
(52) U.S. Cl. ............... 424/145.1; 424/130.1; 424/134.1; 424/141.1; 424/142.1; 514/12
(58) Field of Classification Search ............ None
See application file for complete search history.

(56) References Cited

FOREIGN PATENT DOCUMENTS

| EP | 0 812 913 A2 | 12/1997 |
|---|---|---|
| WO | WO96/04388 | 2/1996 |
| WO | WO97/31946 | 9/1997 |
| WO | WO97/33913 | 9/1997 |
| WO | WO97/47741 | 12/1997 |
| WO | WO97/47742 | 12/1997 |
| WO | WO98/10638 | 3/1998 |

OTHER PUBLICATIONS

E. Choy, Cytokine, vol. 28, pp. 158-161, 2004.*
Borrebaeck et al. Current Opinion in Pharmacology, vol. 1, pp. 404-408, 2001.*
Feldmann et al, 1998. Springer Seminars in Immunopathology, vol. 20, pp. 211-228.*
Aman et al. *J. Biol. Chem.*, 271(46):29265-29270 (1996).
Cheever et al. *J. Immunol.*, 153:753-759 (1994).
Chiaramonte et al. *J. Clin. Invest.*, 104(6):777-785 (1999).
Orchansky et al. *J. Biol. Chem.*, 274(30):20818-20825 (1999).
Zhu et al. *J. Clin. Invest.*, 103(6):779-788 (1999).
Cheever, A.W., "Differential Regulation of Granuloma Size and Hepatic Fibrosis in Schistosome Infections", *Mem. Inst. Oswaldo Cruz*, Rio de Janeiro, 92(5):689-692 (1997).
Chiaramonte et al., "IL-13 is a key regulatory cytokine for Th2 cell-mediated pulmonary granuloma formation and IgE responses induced by *Schistosoma mansoni* eggs", *J. Immunol.*, 162:920-930 (1999), Jan.

* cited by examiner

*Primary Examiner*—Janet L. Andres
*Assistant Examiner*—Fozia Hamud
(74) *Attorney, Agent, or Firm*—Ivor R. Elrifi, Esq.; David E. Johnson, Esq.; Mintz Levin

(57) ABSTRACT

Methods are provided for treating or inhibiting the formation of tissue fibrosis using IL-13 antagonists, including without limitation soluble forms of the IL-13 receptor.

34 Claims, No Drawings

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
      (A) LENGTH: 1525 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (ix) FEATURE:
      (A) NAME/KEY: CDS
      (B) LOCATION: 256..1404

(xi) SEQUENCE DESCRIPTION: SEQ ID NO: 1:

```
GAATTCGGCA CGAGGGAGAG GAGGAGGGAA AGATAGAAAG AGAGAGAGAA AGATTGCTTG        60

CTACCCCTGA ACAGTGACCT CTCTCAAGAC AGTGCTTTGC TCTTCACGTA TAAGGAAGGA       120

AAACAGTAGA GATTCAATTT AGTGTCTAAT GTGGAAAGGA GGACAAAGAG GTCTTGTGAT       180

AACTGCCTGT GATAATACAT TTCTTGAGAA ACCATATTAT TGAGTAGAGC TTTCAGCACA       240

CTAAATCCTG GAGAA ATG GCT TTT GTG CAT ATC AGA TGC TTG TGT TTC ATT       291
                 Met Ala Phe Val His Ile Arg Cys Leu Cys Phe Ile
                  1               5                  10

CTT CTT TGT ACA ATA ACT GGC TAT TCT TTG GAG ATA AAA GTT AAT CCT        339
Leu Leu Cys Thr Ile Thr Gly Tyr Ser Leu Glu Ile Lys Val Asn Pro
            15                  20                  25

CCT CAG GAT TTT GAA ATA TTG GAT CCT GGA TTA CTT GGT TAT CTC TAT        387
Pro Gln Asp Phe Glu Ile Leu Asp Pro Gly Leu Leu Gly Tyr Leu Tyr
        30                  35                  40

TTG CAA TGG AAA CCT CCT GTG GTT ATA GAA AAA TTT AAG GGC TGT ACA        435
Leu Gln Trp Lys Pro Pro Val Val Ile Glu Lys Phe Lys Gly Cys Thr
45                  50                  55                  60

CTA GAA TAT GAG TTA AAA TAC CGA AAT GTT GAT AGC GAC AGC TGG AAG        483
Leu Glu Tyr Glu Leu Lys Tyr Arg Asn Val Asp Ser Asp Ser Trp Lys
                65                  70                  75

ACT ATA ATT ACT AGG AAT CTA ATT TAC AAG GAT GGG TTT GAT CTT AAT        531
Thr Ile Ile Thr Arg Asn Leu Ile Tyr Lys Asp Gly Phe Asp Leu Asn
            80                  85                  90

AAA GGC ATT GAA GGA AAG ATA CGT ACG CAT TTG TCA GAG CAT TGT ACA        579
Lys Gly Ile Glu Gly Lys Ile Arg Thr His Leu Ser Glu His Cys Thr
        95                  100                 105

AAT GGA TCA GAA GTA CAA AGT CCA TGG ATA GAA GCT TCT TAT GGG ATA        627
Asn Gly Ser Glu Val Gln Ser Pro Trp Ile Glu Ala Ser Tyr Gly Ile
    110                 115                 120

TCA GAT GAA GGA AGT TTG GAA ACT AAA ATT CAG GAC ATG AAG TGT ATA        675
Ser Asp Glu Gly Ser Leu Glu Thr Lys Ile Gln Asp Met Lys Cys Ile
125                 130                 135                 140
```

```
TAT TAT AAC TGG CAG TAT TTG GTC TGC TCT TGG AAA CCT GGC AAG ACA       723
Tyr Tyr Asn Trp Gln Tyr Leu Val Cys Ser Trp Lys Pro Gly Lys Thr
                145                 150                 155

GTA TAT TCT GAT ACC AAC TAT ACC ATG TTT TTC TGG TAT GAG GGC TTG       771
Val Tyr Ser Asp Thr Asn Tyr Thr Met Phe Phe Trp Tyr Glu Gly Leu
            160                 165                 170

GAT CAT GCC TTA CAG TGT GCT GAT TAC CTC CAG CAT GAT GAA AAA AAT       819
Asp His Ala Leu Gln Cys Ala Asp Tyr Leu Gln His Asp Glu Lys Asn
        175                 180                 185

GTT GGA TGC AAA CTG TCC AAC TTG GAC TCA TCA GAC TAT AAA GAT TTT       867
Val Gly Cys Lys Leu Ser Asn Leu Asp Ser Ser Asp Tyr Lys Asp Phe
    190                 195                 200

TTT ATC TGT GTT AAT GGA TCT TCA AAG TTG GAA CCC ATC AGA TCC AGC       915
Phe Ile Cys Val Asn Gly Ser Ser Lys Leu Glu Pro Ile Arg Ser Ser
205                 210                 215                 220

TAT ACA GTT TTT CAA CTT CAA AAT ATA GTT AAA CCA TTG CCA CCA GAA       963
Tyr Thr Val Phe Gln Leu Gln Asn Ile Val Lys Pro Leu Pro Pro Glu
                225                 230                 235

TTC CTT CAT ATT AGT GTG GAG AAT TCC ATT GAT ATT AGA ATG AAA TGG      1011
Phe Leu His Ile Ser Val Glu Asn Ser Ile Asp Ile Arg Met Lys Trp
            240                 245                 250

AGC ACA CCT GGA GGA CCC ATT CCA CCA AGG TGT TAC ACT TAT GAA ATT      1059
Ser Thr Pro Gly Gly Pro Ile Pro Pro Arg Cys Tyr Thr Tyr Glu Ile
        255                 260                 265

GTG ATC CGA GAA GAC GAT ATT TCC TGG GAG TCT GCC ACA GAC AAA AAC      1107
Val Ile Arg Glu Asp Asp Ile Ser Trp Glu Ser Ala Thr Asp Lys Asn
    270                 275                 280

GAT ATG AAG TTG AAG AGG AGA GCA AAT GAA AGT GAA GAC CTA TGC TTT      1155
Asp Met Lys Leu Lys Arg Arg Ala Asn Glu Ser Glu Asp Leu Cys Phe
285                 290                 295                 300

TTT GTA AGA TGT AAG GTC AAT ATA TAT TGT GCA GAT GAT GGA ATT TGG      1203
Phe Val Arg Cys Lys Val Asn Ile Tyr Cys Ala Asp Asp Gly Ile Trp
                305                 310                 315

AGC GAA TGG AGT GAA GAG GAA TGT TGG GAA GGT TAC ACA GGG CCA GAC      1251
Ser Glu Trp Ser Glu Glu Glu Cys Trp Glu Gly Tyr Thr Gly Pro Asp
            320                 325                 330

TCA AAG ATT ATT TTC ATA GTA CCA GTT TGT CTT TTC TTT ATA TTC CTT      1299
Ser Lys Ile Ile Phe Ile Val Pro Val Cys Leu Phe Phe Ile Phe Leu
        335                 340                 345

TTG TTA CTT CTT TGC CTT ATT GTG GAG AAG GAA GAA CCT GAA CCC ACA      1347
Leu Leu Leu Leu Cys Leu Ile Val Glu Lys Glu Glu Pro Glu Pro Thr
    350                 355                 360

TTG AGC CTC CAT GTG GAT CTG AAC AAA GAA GTG TGT GCT TAT GAA GAT      1395
Leu Ser Leu His Val Asp Leu Asn Lys Glu Val Cys Ala Tyr Glu Asp
365                 370                 375                 380

ACC CTC TGT TAAACCACCA ATTTCTTGAC ATAGAGCCAG CCAGCAGGAG              1444
Thr Leu Cys

TCATATTAAA CTCAATTTCT CTTAAAATTT CGAATACATC TTCTTGAAAA TCCAAAAAAA    1504

AAAAAAAAAA AAAAACTCGA G                                              1525

(2) INFORMATION FOR SEQ ID NO: 2:

(i) SEQUENCE CHARACTERISTICS:
        (A) LENGTH: 383 amino acids
        (B) TYPE: amino acid
        (D) TOPOLOGY: linear (ii) MOLECULE TYPE: protein (xi) SEQUENCE DESCRIPTION: SEQ ID NO: 2:
```

```
Met Ala Phe Val His Ile Arg Cys Leu Cys Phe Ile Leu Leu Cys Thr
 1               5                  10                  15

Ile Thr Gly Tyr Ser Leu Glu Ile Lys Val Asn Pro Pro Gln Asp Phe
                20                  25                  30

Glu Ile Leu Asp Pro Gly Leu Gly Tyr Leu Tyr Leu Gln Trp Lys
             35                  40                  45

Pro Pro Val Val Ile Glu Lys Phe Lys Gly Cys Thr Leu Glu Tyr Glu
         50                  55                  60

Leu Lys Tyr Arg Asn Val Asp Ser Asp Ser Trp Lys Thr Ile Ile Thr
 65                  70                  75                  80

Arg Asn Leu Ile Tyr Lys Asp Gly Phe Asp Leu Asn Lys Gly Ile Glu
                 85                  90                  95

Gly Lys Ile Arg Thr His Leu Ser Glu His Cys Thr Asn Gly Ser Glu
            100                 105                 110

Val Gln Ser Pro Trp Ile Glu Ala Ser Tyr Gly Ile Ser Asp Glu Gly
        115                 120                 125

Ser Leu Glu Thr Lys Ile Gln Asp Met Lys Cys Ile Tyr Tyr Asn Trp
130                 135                 140

Gln Tyr Leu Val Cys Ser Trp Lys Pro Gly Lys Thr Val Tyr Ser Asp
145                 150                 155                 160

Thr Asn Tyr Thr Met Phe Phe Trp Tyr Glu Gly Leu Asp His Ala Leu
                165                 170                 175

Gln Cys Ala Asp Tyr Leu Gln His Asp Glu Lys Asn Val Gly Cys Lys
            180                 185                 190

Leu Ser Asn Leu Asp Ser Ser Asp Tyr Lys Asp Phe Phe Ile Cys Val
            195                 200                 205

Asn Gly Ser Ser Lys Leu Glu Pro Ile Arg Ser Ser Tyr Thr Val Phe
210                 215                 220

Gln Leu Gln Asn Ile Val Lys Pro Leu Pro Pro Glu Phe Leu His Ile
225                 230                 235                 240

Ser Val Glu Asn Ser Ile Asp Ile Arg Met Lys Trp Ser Thr Pro Gly
                245                 250                 255

Gly Pro Ile Pro Pro Arg Cys Tyr Thr Tyr Glu Ile Val Ile Arg Glu
                260                 265                 270

Asp Asp Ile Ser Trp Glu Ser Ala Thr Asp Lys Asn Asp Met Lys Leu
            275                 280                 285

Lys Arg Arg Ala Asn Glu Ser Glu Asp Leu Cys Phe Phe Val Arg Cys
290                 295                 300

Lys Val Asn Ile Tyr Cys Ala Asp Asp Gly Ile Trp Ser Glu Trp Ser
305                 310                 315                 320

Glu Glu Glu Cys Trp Glu Gly Tyr Thr Gly Pro Asp Ser Lys Ile Ile
                325                 330                 335

Phe Ile Val Pro Val Cys Leu Phe Phe Ile Phe Leu Leu Leu Leu Leu
            340                 345                 350

Cys Leu Ile Val Glu Lys Glu Glu Pro Glu Pro Thr Leu Ser Leu His
            355                 360                 365

Val Asp Leu Asn Lys Glu Val Cys Ala Tyr Glu Asp Thr Leu Cys
370                 375                 380
```

(2) INFORMATION FOR SEQ ID NO: 3:

(i) SEQUENCE CHARACTERISTICS:
       (A) LENGTH: 1369 base pairs
       (B) TYPE: nucleic acid (C) STRANDEDNESS: double
(D) TOPOLOGY: linear (ii) MOLECULE TYPE: cDNA (iii) HYPOTHETICAL: NO (ix) FEATURE:
    (A) NAME/KEY: CDS
    (B) LOCATION: 103..1245

(xi) SEQUENCE DESCRIPTION: SEQ ID NO: 3:

| | |
|---|---|
| GGATCCGCGC GGATGAAGGC TATTTGAAGT CGCCATAACC TGGTCAGAAG TGTGCCTGTC | 60 |
| GGCGGGGAGA GAGGCAATAT CAAGGTTTTA AATCTCGGAG AA ATG GCT TTC GTT<br>                              Met Ala Phe Val<br>                               1 | 114 |
| TGC TTG GCT ATC GGA TGC TTA TAT ACC TTT CTG ATA AGC ACA ACA TTT<br>Cys Leu Ala Ile Gly Cys Leu Tyr Thr Phe Leu Ile Ser Thr Thr Phe<br>5          10          15          20 | 162 |
| GGC TGT ACT TCA TCT TCA GAC ACC GAG ATA AAA GTT AAC CCT CCT CAG<br>Gly Cys Thr Ser Ser Ser Asp Thr Glu Ile Lys Val Asn Pro Pro Gln<br>        25          30          35 | 210 |
| GAT TTT GAG ATA GTG GAT CCC GGA TAC TTA GGT TAT CTC TAT TTG CAA<br>Asp Phe Glu Ile Val Asp Pro Gly Tyr Leu Gly Tyr Leu Tyr Leu Gln<br>      40          45          50 | 258 |
| TGG CAA CCC CCA CTG TCT CTG GAT CAT TTT AAG GAA TGC ACA GTG GAA<br>Trp Gln Pro Pro Leu Ser Leu Asp His Phe Lys Glu Cys Thr Val Glu<br>   55          60          65 | 306 |
| TAT GAA CTA AAA TAC CGA AAC ATT GGT AGT GAA ACA TGG AAG ACC ATC<br>Tyr Glu Leu Lys Tyr Arg Asn Ile Gly Ser Glu Thr Trp Lys Thr Ile<br>70          75          80 | 354 |
| ATT ACT AAG AAT CTA CAT TAC AAA GAT GGG TTT GAT CTT AAC AAG GGC<br>Ile Thr Lys Asn Leu His Tyr Lys Asp Gly Phe Asp Leu Asn Lys Gly<br>85          90          95         100 | 402 |
| ATT GAA GCG AAG ATA CAC ACG CTT TTA CCA TGG CAA TGC ACA AAT GGA<br>Ile Glu Ala Lys Ile His Thr Leu Leu Pro Trp Gln Cys Thr Asn Gly<br>        105          110         115 | 450 |
| TCA GAA GTT CAA AGT TCC TGG GCA GAA ACT ACT TAT TGG ATA TCA CCA<br>Ser Glu Val Gln Ser Ser Trp Ala Glu Thr Thr Tyr Trp Ile Ser Pro<br>      120          125          130 | 498 |
| CAA GGA ATT CCA GAA ACT AAA GTT CAG GAT ATG GAT TGC GTA TAT TAC<br>Gln Gly Ile Pro Glu Thr Lys Val Gln Asp Met Asp Cys Val Tyr Tyr<br>   135          140          145 | 546 |
| AAT TGG CAA TAT TTA CTC TGT TCT TGG AAA CCT GGC ATA GGT GTA CTT<br>Asn Trp Gln Tyr Leu Leu Cys Ser Trp Lys Pro Gly Ile Gly Val Leu<br>150          155          160 | 594 |
| CTT GAT ACC AAT TAC AAC TTG TTT TAC TGG TAT GAG GGC TTG GAT CAT<br>Leu Asp Thr Asn Tyr Asn Leu Phe Tyr Trp Tyr Glu Gly Leu Asp His<br>165          170          175         180 | 642 |
| GCA TTA CAG TGT GTT GAT TAC ATC AAG GCT GAT GGA CAA AAT ATA GGA<br>Ala Leu Gln Cys Val Asp Tyr Ile Lys Ala Asp Gly Gln Asn Ile Gly<br>        185          190         195 | 690 |
| TGC AGA TTT CCC TAT TTG GAG GCA TCA GAC TAT AAA GAT TTC TAT ATT<br>Cys Arg Phe Pro Tyr Leu Glu Ala Ser Asp Tyr Lys Asp Phe Tyr Ile<br>      200          205          210 | 738 |
| TGT GTT AAT GGA TCA TCA GAG AAC AAG CCT ATC AGA TCC AGT TAT TTC<br>Cys Val Asn Gly Ser Ser Glu Asn Lys Pro Ile Arg Ser Ser Tyr Phe<br>   215          220          225 | 786 |
| ACT TTT CAG CTT CAA AAT ATA GTT AAA CCT TTG CCG CCA GTC TAT CTT<br>Thr Phe Gln Leu Gln Asn Ile Val Lys Pro Leu Pro Pro Val Tyr Leu<br>230          235          240 | 834 |

```
ACT TTT ACT CGG GAG AGT TCA TGT GAA ATT AAG CTG AAA TGG AGC ATA      882
Thr Phe Thr Arg Glu Ser Ser Cys Glu Ile Lys Leu Lys Trp Ser Ile
245                 250                 255                 260

CCT TTG GGA CCT ATT CCA GCA AGG TGT TTT GAT TAT GAA ATT GAG ATC      930
Pro Leu Gly Pro Ile Pro Ala Arg Cys Phe Asp Tyr Glu Ile Glu Ile
                265                 270                 275

AGA GAA GAT GAT ACT ACC TTG GTG ACT GCT ACA GTT GAA AAT GAA ACA      978
Arg Glu Asp Asp Thr Thr Leu Val Thr Ala Thr Val Glu Asn Glu Thr
            280                 285                 290

TAC ACC TTG AAA ACA ACA AAT GAA ACC CGA CAA TTA TGC TTT GTA GTA     1026
Tyr Thr Leu Lys Thr Thr Asn Glu Thr Arg Gln Leu Cys Phe Val Val
        295                 300                 305

AGA AGC AAA GTG AAT ATT TAT TGC TCA GAT GAC GGA ATT TGG AGT GAG     1074
Arg Ser Lys Val Asn Ile Tyr Cys Ser Asp Asp Gly Ile Trp Ser Glu
    310                 315                 320

TGG AGT GAT AAA CAA TGC TGG GAA GGT GAA GAC CTA TCG AAG AAA ACT     1122
Trp Ser Asp Lys Gln Cys Trp Glu Gly Glu Asp Leu Ser Lys Lys Thr
325                 330                 335                 340

TTG CTA CGT TTC TGG CTA CCA TTT GGT TTC ATC TTA ATA TTA GTT ATA     1170
Leu Leu Arg Phe Trp Leu Pro Phe Gly Phe Ile Leu Ile Leu Val Ile
                345                 350                 355

TTT GTA ACC GGT CTG CTT TTG CGT AAG CCA AAC ACC TAC CCA AAA ATG     1218
Phe Val Thr Gly Leu Leu Leu Arg Lys Pro Asn Thr Tyr Pro Lys Met
                360                 365                 370

ATT CCA GAA TTT TTC TGT GAT ACA TGA AGACTTTCCA TATCAAGAGA           1265
Ile Pro Glu Phe Phe Cys Asp Thr *
            375                 380

CATGGTATTG ACTCAACAGT TCCAGTCAT GGCCAAATGT TCAATATGAG TCTCAATAAA    1325

CTGAATTTTT CTTGCGAAAA AAAAAAAAAA AAATCCGCGG ATCC                    1369

(2) INFORMATION FOR SEQ ID NO: 4:

(i) SEQUENCE CHARACTERISTICS:
        (A) LENGTH: 380 amino acids
        (B) TYPE: amino acid
        (D) TOPOLOGY: linear (ii) MOLECULE TYPE: protein (xi) SEQUENCE DESCRIPTION: SEQ ID NO: 4:

Met Ala Phe Val Cys Leu Ala Ile Gly Cys Leu Tyr Thr Phe Leu Ile
 1               5                  10                  15

Ser Thr Thr Phe Gly Cys Thr Ser Ser Asp Thr Glu Ile Lys Val
            20                  25                  30

Asn Pro Pro Gln Asp Phe Glu Ile Val Asp Pro Gly Tyr Leu Gly Tyr
        35                  40                  45

Leu Tyr Leu Gln Trp Gln Pro Pro Leu Ser Leu Asp His Phe Lys Glu
    50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
        115                 120                 125

Trp Ile Ser Pro Gln Gly Ile Pro Glu Thr Lys Val Gln Asp Met Asp
    130                 135                 140
```

```
Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
        195                 200                 205

Asp Phe Tyr Ile Cys Val Asn Gly Ser Ser Glu Asn Lys Pro Ile Arg
    210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
        275                 280                 285

Glu Asn Glu Thr Tyr Thr Leu Lys Thr Thr Asn Glu Thr Arg Gln Leu
    290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                325                 330                 335

Ser Lys Lys Thr Leu Leu Arg Phe Trp Leu Pro Phe Gly Phe Ile Leu
            340                 345                 350

Ile Leu Val Ile Phe Val Thr Gly Leu Leu Leu Arg Lys Pro Asn Thr
        355                 360                 365

Tyr Pro Lys Met Ile Pro Glu Phe Phe Cys Asp Thr
370                 375                 380

(2) INFORMATION FOR SEQ ID NO: 5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 5:

KSRCTCCABK CRCTCCA                                                   17

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 6:

ATAGTTAAAC CATTGCCACC                                                20

(2) INFORMATION FOR SEQ ID NO: 7:

(i) SEQUENCE CHARACTERISTICS:
```

```
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 7:

CTCCATTCGC TCCAAATTCC                                          20

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 8:

AGTCTATCTT ACTTTTACTC G                                        21

(2) INFORMATION FOR SEQ ID NO: 9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 9:

CATCTGAGCA ATAAATATTC AC                                       22
```

TREATMENT OF FIBROSIS BY ANTAGONISM OF IL-13 AND IL-13 RECEPTOR CHAINS

This application is a divisional application of application Ser. No. 09/301,808, filed Apr. 28, 1999, now U.S. Pat. No. 6,664,227. The contents of this application are incorporated by reference in their entirety.

FIELD OF THE INVENTION

The present invention relates to the treatment and inhibition of fibrosis by antagonism of the interaction of IL-13 with its receptor and receptor components.

BACKGROUND OF THE INVENTION

A variety of regulatory molecules, known as cytokines, have been identified including interleuklin-13 (IL-13). Various protein forms of IL-13 and DNA encoding various forms of IL-13 activity are described in McKenzie et al., Proc. Natl. Acad. Sci. USA 90:3735 (1993); Minty et al., Nature 362:248 (1993); and Aversa et al., WO94/04680. Thus, the term "IL-13" includes proteins having the sequence and/or biological activity described in these documents, whether produced by recombinant genetic engineering techniques; purified from cell sources producing the factor naturally or upon induction with other factors; or synthesized by chemical techniques; or a combination of the foregoing.

IL-13 is a cytokine that has been implicated in production of several biological activities including: induction of IgG4 and IgE switching, including in human immature B cells (Punnonen et al., J. Immunol. 152:1094 (1994)); induction of germ line IgE heavy chain ($\epsilon$) transcription and CD23 expression in normal human B cells (Punnonen et al., Proc. Natl. Acad. Sci. USA 90:3730 (1993)); and induction of B cell proliferation in the presence of CD40L or anti-CD40 mAb (Cocks et al., Int. Immunol. 5:657 (1993)). Although many activities of IL-13 are similar to those of IL4, in contrast to L-4, IL-13 does not have growth promoting effects on activated T cells or T cell clones (Zurawski et al., EMBO J. 12:2663 (1993)).

Like most cytokines, IL-13 exhibits certain biological activities by interacting with an IL-13 receptor ("IL-13R") on the surface of target cells. IL-13R and the IL-4 receptor ("IL-4R") sharing a common component, which is required for receptor activation; however, L-13 does not bind to cells transfected with the 130 kD IL-4R (Zurawski et al., supra). Thus, the IL-13R must contain at least one other ligand binding chain. Cytokine receptors are commonly composed or two or three chains. The cloning of one ligand binding chain for IL-13 has been recently reported (Hilton et al., Proc. Natl. Acad. Sci. 93:497–501).

It would be desirable to identify and clone the sequence for any other L-13 binding chain of IL-13R so that IL-13R proteins can be produced for various reasons, including production of therapeutics and screening for inhibitors of IL-13 binding to the receptor and receptor signaling.

SUMMARY OF THE INVENTION

In accordance with the present invention, polynucleotides encoding the IL-13 binding chains of the interleukin-13 receptor are disclosed, including without limitation those from the murine and human receptors. In certain embodiments, the invention provides an isolated polynucleotide comprising a nucleotide sequence selected from the group consisting of:

(a) the nucleotide sequence of SEQ ID NO: 1 from nucleotide 256 to nucleotide 1404;
(b) the nucleotide sequence of SEQ ID NO:3 from nucleotide 103 to nucleotide 1242;
(c) a nucleotide sequence varying from the sequence of the nucleotide sequence specified in (a) or (b) as a result of degeneracy of the genetic code;
(d) a nucleotide sequence capable of hybridizing under stringent conditions to the nucleotide specified in (a) or (b);
(e) a nucleotide sequence encoding a species homologue of the sequence specified in (a) or (b); and
(f) an allelic variant of the nucleotide sequence specified in (a) or (b).

Preferably, the nucleotide sequence encodes a protein having a biological activity of the human IL-13 receptor. The nucleotide sequence may be operably linked to an expression control sequence. In preferred embodiments, the polynucleotide comprises the nucleotide sequence of SEQ ID NO:1 from nucleotide 256 to nucleotide 1404; the nucleotide sequence of SEQ ID NO:1 from nucleotide 319 to nucleotide 1257; the nucleotide sequence of SEQ ID NO:1 from nucleotide 1324 to nucleotide 1404; the nucleotide sequence of SEQ ID NO:3 from nucleotide 103 to nucleotide 1242; the nucleotide sequence of SEQ ID NO:3 from nucleotide 178 to nucleotide 1125; or the nucleotide sequence of SEQ ID NO:3 from nucleotide 1189 to nucleotide 1242.

The invention also provides isolated polynucleotides comprising a nucleotide sequence encoding a peptide or protein comprising an amino acid sequence selected from the group consisting of:

(a) the amino acid sequence of SEQ ID NO:2;
(b) the amino acid sequence of SEQ ID NO:2 from amino acids 22 to 334;
(c) the amino acid sequence of SEQ ID NO:2 from amino acids 357 to 383;
(d) the amino acid sequence of SEQ ID NO:4;
(e) the amino acid sequence of SEQ ID NO:4 from amino acids 26 to 341;
(f) the amino acid sequence of SEQ ID NO:4 from amino acids 363 to 380; and
(g) fragments of (a)–(f) having a biological activity of the IL-13 receptor binding chain. Other preferred embodiments encode the amino acid sequence of SEQ ID NO:2 from amino acids 1 to 331 and the amino acid sequence of SEQ ID NO:2 from amino acids 26 to 331.

Host cells, preferably mammalian cells, transformed with the polynucleotides are also provided.

In other embodiments, the invention provides a process for producing a IL-13bc protein. The process comprises:

(a) growing a culture of the host cell of the present invention in a suitable culture medium; and
(b) purifying the human IL-13bc protein from the culture.

Proteins produced according to these methods are also provided.

The present invention also provides for an isolated IL-13bc protein comprising an amino acid sequence selected from the group consisting of:

(a) the amino acid sequence of SEQ ID NO:2;
(b) the amino acid sequence of SEQ ID NO:2 from amino acids 22 to 334;
(c) the amino acid sequence of SEQ ID NO:2 from amino acids 357 to 383;
(d) the amino acid sequence of SEQ ID NO:4;
(e) the amino acid sequence of SEQ ID NO:4 from amino acids 26 to 341;

(f) the amino acid sequence of SEQ ID NO:4 from amino acids 363 to 380; and (g) fragments of (a)–(f) having a biological activity of the IL-13 receptor binding chain.

Preferably the protein comprises the amino acid sequence of SEQ ID NO:2; the sequence from amino acid 22 to 334 of SEQ ID NO:2; the sequence of SEQ ID NO:4; or the sequence from amino acid 26 to 341 of SEQ ID NO:4. In other preferred embodiments, the specified amino acid sequence is part of a fusion protein (with an additional amino acid sequence not derived from IL-13bc). Preferred fusion proteins comprise an antibody fragment, such as an Fc fragment. Particularly preferred embodiments comprise the amino acid sequence of SEQ ID NO:2 from amino acids 1 to 331 and the amino acid sequence of SEQ ID NO:2 from amino acids 26 to 331.

Pharmaceutical compositions comprising a protein of the present invention and a pharmaceutically acceptable carrier are also provided.

The present invention further provides for compositions comprising an antibody which specifically reacts with a protein of the present invention.

Methods of identifying an inhibitor of IL-13 binding to the IL-13bc or IL-13 receptor are also provided. These methods comprise:

(a) combining an IL-13bc protein or a fragment thereof with IL-13 or a fragment thereof, said combination forming a first binding mixture;

(b) measuring the amount of binding between the protein and the IL-13 or fragment in the first binding mixture;

(c) combining a compound with the protein and the IL-13 or fragment to form a second binding mixture;

(d) measuring the amount of binding in the second binding mixture; and (e) comparing the amount of binding in the first binding mixture with the amount of binding in the second binding mixture;

wherein the compound is capable of inhibiting IL-13 binding to the IL-13bc protein or IL-13 receptor when a decrease in the amount of binding of the second binding mixture occurs. Inhibitors of IL-13R identified by these methods and pharmaceutical compositions containing them are also provided.

Methods of inhibiting binding of IL-13 to the IL-13bc proteins or IL-13 receptor in a mammalian subject are also disclosed which comprise administering a therapeutically effective amount of a composition containing an IL-13bc protein, an IL-13bc or IL-13R inhibitor or an antibody to an IL-13bc protein.

Methods are also provided for potentiating IL-13 activity, which comprise combining a protein having IL-13 activity with a protein of the present invention and contacting such combination with a cell expressing at least one chain of IL-13R other than IL-13bc. Preferably, the contacting step is performed by administering a therapeutically effective amount of such combination to a mammalian subject.

Further methods are provided for treating an IL-13-related condition in a mammalian subject, said method comprising administering a therapeutically effective amount of a composition comprising an IL-13 antagonist and a pharmaceutically acceptable carrier. Other methods provide for a method of inhibiting the interaction of IL-13 with an IL-13bc protein in a mammalian subject comprising administering a therapeutically effective amount of a composition comprising an IL-13 antagonist and a pharmaceutically acceptable carrier. Preferably, the antagonist is selected from the group consisting of an IL-13bc protein, a soluble form of IL-13Rα1, an antibody to IL-13 or an IL-13-binding fragment thereof, an antibody to IL-13bc or an IL-13bc-binding fragment thereof, an antibody to IL-13Rα1 or an IL-13Rα1-binding fragment thereof, IL-13R-binding mutants of IL-4, a small molecule capable of inhibiting the interaction of IL-13 with IL-13bc and a small molecule capable of inhibiting the interaction of IL-13 with IL-13Rα1.

In yet other embodiments, the invention provides for a method of treating tissue fibrosis in a mammalian subject. The method comprises administering a therapeutically effective amount of a pharmaceutical composition comprising a protein and a pharmaceutically acceptable carrier, wherein the protein comprises an amino acid sequence selected from the group consisting of:

(a) the amino acid sequence of SEQ ID NO:2;

(b) the amino acid sequence of SEQ ID NO:2 from amino acids 22 to 334;

(c) the amino acid sequence of SEQ ID NO:2 from amino acids 357 to 383;

(d) the amino acid sequence of SEQ ID NO:4;

(e) the amino acid sequence of SEQ ID NO:4 from amino acids 26 to 341;

(f) the amino acid sequence of SEQ ID NO:4 from amino acids 363 to 380; and (g) fragments of (a)–(f) having a biological activity of the IL-13 receptor binding chain.

The invention also provides for a method of inhibiting formation of tissue fibrosis in a mammalian subject. The method comprises administering a therapeutically effective amount of a pharmaceutical composition comprising a protein and a pharmaceutically acceptable carrier, wherein the protein comprises an amino acid sequence selected from the group consisting of:

(a) the amino acid sequence of SEQ ID NO:2;

(b) the amino acid sequence of SEQ ID NO:2 from amino acids 22 to 334;

(c) the amino acid sequence of SEQ ID NO:2 from amino acids 357 to 383;

(d) the amino acid sequence of SEQ ID NO:4;

(e) the amino acid sequence of SEQ ID NO:4 from amino acids 26 to 341;

(f) the amino acid sequence of SEQ ID NO:4 from amino acids 363 to 380; and (g) fragments of (a)–(f) having a biological activity of the IL-13 receptor binding chain.

Other embodiments of the invention provide for a method of treating or inhibiting tissue fibrosis in a mammalian subject. The method comprises administering a therapeutically effective amount of a composition comprising (a) a molecule selected from the group consisting of an IL-13 antagonist and an IL-4 antagonist, and (b) a pharmaceutically acceptable carrier.

In practicing such methods of treating or inhibiting fibrosis, preferably the tissue fibrosis affects a tissue selected from the group consisting of liver, skin epidermis, skin endodermis, muscle, tendon, cartilage, cardiac tissue, pancreatic tissue, lung tissue, uterine tissue, neural tissue, testis, ovary, adrenal gland, artery, vein, colon, small intestine, biliary tract and gut; most preferably, liver tissue (including tissue infected with *schistosoma*). In certain embodiments, the fibrois results from the healing of a wound (including a surgical incision).

In practicing such methods of treating or inhibiting fibrosis using an antagonist, preferably such antagonist is selected from the group consisting of an IL-13bc protein, a soluble form of IL-13Rα1, an antibody to IL-13 or an IL-13-binding fragment thereof, an antibody to IL-13bc or an IL-13bc-binding fragment thereof, an antibody to IL-13Rα1 or an IL-13Rα1-binding fragment thereof, IL-13R-binding mutants of IL4, a small molecule capable of inhibiting the interaction of IL-13 with IL-13bc and a small molecule capable of inhibiting the interaction of IL-13 with IL-13Rα1. In particularly preferred embodiments, the antagonist is an IL-13bc protein comprising an amino acid sequence selected from the group consisting of:

(a) the amino acid sequence of SEQ ID NO:2;

(b) the amino acid sequence of SEQ ID NO:2 from amino acids 22 to 334;

(c) the amino acid sequence of SEQ ID NO:2 from amino acids 357 to 383;

(d) the amino acid sequence of SEQ ID NO:4;

(e) the amino acid sequence of SEQ ID NO:4 from amino acids 26 to 341;

(f) the amino acid sequence of SEQ ID NO:4 from amino acids 363 to 380; and (g) fragments of (a)–(f) having a biological activity of the IL-13 receptor binding chain.

In other preferred methods of practicing such methods using an antagonist the antagonist is selected from the group consisting of a soluble form of IL-4R, an antibody to IL-4 or an IL-4-binding fragment thereof, an antibody to IL-4R or an IL-4R-binding fragment thereof, and a small molecule capable of inhibiting the interaction of IL-4 with IL-4R.

DETAILED DESCRIPTION OF PREFERRED EMBODIMENTS

The inventors of the present application have for the first time identified and provided polynucleotides encoding the IL-13 binding chain of IL-13R (hereinafter "IL-13bc"), including without limitation polynucleotides encoding murine and human IL-13bc.

SEQ ID NO:1 provides the nucleotide sequence of a cDNA encoding the murine IL-13bc. SEQ ID NO:2 provides predicted the amino acid sequence of the receptor chain, including a putative signal sequence from amino acids 1–21. The mature murine IL-13bc is believed to have the sequence of amino acids 22–383 of SEQ ID NO:2. The mature murine receptor chain has at least three distinct domains: an extracellular domain (comprising approximately amino acids 22–334 of SEQ ID NO:2), a transmembrane domain (comprising approximately amino acids 335–356 of SEQ ID NO:2) and an intracellular domain (comprising approximately amino acids 357–383 of SEQ ID NO:2).

SEQ ID NO:3 provides the nucleotide sequence of a cDNA encoding the human IL-13bc. SEQ ID NO:4 provides predicted the amino acid sequence of the receptor chain, including a putative signal sequence from amino acids 1–25. The mature human IL-13bc is believed to have the sequence of amino acids 26–380 of SEQ ID NO:4. The mature human receptor chain has at least three distinct domains: an extracellular domain (comprising approximately amino acids 26–341 of SEQ ID NO:4), a transmembrane domain (comprising approximately amino acids 342–362 of SEQ ID NO:4) and an intracellular domain (comprising approximately amino acids 363–380 of SEQ ID NO:4).

The first 81 amino acids of the human IL-13bc sequence are identical to the translated sequence of an expressed sequence tag (EST) identified as "yg99f10.r1 *Homo sapiens* cDNA clone 41648 5'" and assigned database accession number R52795.gb_est2. There are no homologies or sequence motifs in this EST sequence which would lead those skilled in the art to identify the encoded protein as a cytokine receptor. A cDNA clone corresponding to this database entry is publicly-available from the I.M.A.G.E. Consortium. Subsequent to the priority date of the present application, such clone was ordered by applicants and sequenced. The sequence of such clone was determined to be the sequence previously reported by applicants as SEQ ID NO:3 herein.

Soluble forms of IL-13bc protein can also be produced. Such soluble forms include without limitation proteins comprising amino acids 1–334 or 22–334 of SEQ ID NO:2 or amino acids 1–341 or 26–341 of SEQ ID NO:4. The soluble forms of the IL-13bc are further characterized by being soluble in aqueous solution, preferably at room temperature. IL-13bc proteins comprising only the intracellular domain or a portion thereof may also be produced. Any forms of IL-13bc of less than full length are encompassed within the present invention and are referred to herein collectively with full length and mature forms as "IL-13bc" or "IL-13bc proteins." IL-13bc proteins of less than full length may be produced by expressing a corresponding fragment of the polynucleotide encoding the full-length IL-13bc protein (SEQ ID NO:1 or SEQ ID NO:3). These corresponding polynucleotide fragments are also part of the present invention. Modified polynucleotides as described above may be made by standard molecular biology techniques, including construction of appropriate desired deletion mutants, site-directed mutagenesis methods or by the polymerase chain reaction using appropriate oligonucleotide primers.

For the purposes of the present invention, a protein has "a biological activity of the IL-13 receptor binding chain" if it possess one or more of the following characteristics: (I) the ability to bind IL-13 or a fragment thereof (preferably a biologically active fragment thereof); and/or (2) the ability to interact with the second non-IL-13-binding chain of IL-13R to produce a signal characteristic of the binding of IL-13 to IL-13R. Preferably, the biological activity possessed by the protein is the ability to bind IL-13 or a fragment hereof, more preferably with a $K_D$ of about 0.1 to about 100 nM. Methods for determining whether a particular protein or peptide has such activity include without limitation the methods described in the examples provided herein.

IL-13bc or active fragments thereof (IL-13bc proteins) may be fused to carrier molecules such as immunoglobulins. For example, soluble forms of the IL-13bc may be fused through "linker" sequences to the Fc portion of an immunoglobulin. Other fusions proteins, such as those with GST, Lex-A or MBP, may also be used.

The invention also encompasses allelic variants of the nucleotide sequences as set forth in SEQ ID NO:1 or SEQ ID NO:3, that is, naturally-occurring alternative forms of the isolated polynucleotide of SEQ ID NO:1 or SEQ ID NO:3 which also encode IL-13bc proteins, preferably those proteins having a biological activity of IL-13bc. Also included in the invention are isolated polynucleotides which hybridize to the nucleotide sequence set forth in SEQ ID NO:1 or SEQ ID NO:3 under highly stringent conditions (for example, 0.1×SSC at 65° C.). Isolated polynucleotides which encode IL-13bc proteins but which differ from the nucleotide sequence set forth in SEQ ID NO:1 or SEQ ID NO:3 by virtue of the degeneracy of the genetic code are also encompassed by the present invention. Variations in the nucleotide sequence as set forth in SEQ ID NO:1 or SEQ ID NO:3 which are caused by point mutations or by induced modifications are also included in the invention.

The present invention also provides polynucleotides encoding homologues of the murine and human IL-13bc from other animal species, particularly other mammalian species. Species homologues can be identified and isolated by making probes or primers from the murine or human sequences disclosed herein and screening a library from an appropriate species, such as for example libraries constructed from PBMCs, thymus or testis of the relevant species.

The isolated polynucleotides of the invention may be operably linked to an expression control sequence such as the pMT2 or pED expression vectors disclosed in Kaufman et al., Nucleic Acids Res. 19, 4485–4490 (1991), in order to produce the IL-13bc protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means enzymatically or chemically ligated to form a covalent bond between the isolated polynucleotide of the invention and the expression control sequence, in such a way that the IL-13bc protein is expressed by a host cell which has been transformed (transfected) with the ligated polynucleotide/expression control sequence.

A number of types of cells may act as suitable host cells for expression of the IL-13bc protein. Any cell type capable of expressing functional IL-13bc protein may be used. Suitable mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK, Rat2, BaF3, 32D, FDCP-1, PC12, MIx or C2C12 cells.

The IL-13bc protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No.* 1555 (1987), incorporated herein by reference. Soluble forms of the IL-13bc protein may also be produced in insect cells using appropriate isolated polynucleotides as described above.

Alternatively, the IL-13bc protein may be produced in lower eukaryotes such as yeast or in prokaryotes such as bacteria. Suitable yeast strains include *Saccharomyces cerevisiae, Schizosaccharomyces pombe, Kluyveromyces* strains, *Candida*, or any yeast strain capable of expressing heterologous proteins. Suitable bacterial strains include *Escherichia coli, Bacillus subtilis, Salmonella typhimurium*, or any bacterial strain capable of expressing heterologous proteins.

Expression in bacteria may result in formation of inclusion bodies incorporating the recombinant protein. Thus, refolding of the recombinant protein may be required in order to produce active or more active material. Several methods for obtaining correctly folded heterologous proteins from bacterial inclusion bodies are known in the art. These methods generally involve solubilizing the protein from the inclusion bodies, then denaturing the protein completely using a chaotropic agent. When cysteine residues are present in the primary amino acid sequence of the protein, it is often necessary to accomplish the refolding in an environment which allows correct formation of disulfide bonds (a redox system). General methods of refolding are disclosed in Kohno, *Meth. Enzym.*, 185:187–195 (1990). EP 0433225 and copending application U.S. Ser. No. 08/163,877 describe other appropriate methods.

The IL-13bc protein of the invention may also be expressed as a product of transgenic animals, e.g., as a component of the milk of transgenic cows, goats, pigs, or sheep which are characterized by somatic or germ cells containing a polynucleotide sequence encoding the IL-13bc protein.

The IL-13bc protein of the invention may be prepared by growing a culture transformed host cells under culture conditions necessary to express the desired protein. The resulting expressed protein may then be purified from the culture medium or cell extracts. Soluble forms of the IL-13bc protein of the invention can be purified from conditioned media. Membrane-bound forms of IL-13bc protein of the invention can be purified by preparing a total membrane fraction from the expressing cell and extracting the membranes with a non-ionic detergent such as Triton X-100.

The IL-13bc protein can be purified using methods known to those skilled in the art. For example, the IL-13bc protein of the invention can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) or polyetheyleneimine (PEI) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred (e.g., S-Sepharose® columns). The purification of the IL-13bc protein from culture supernatant may also include one or more column steps over such affinity resins as concanavalin A-agarose, heparin-toyopearl® or Cibacrom blue 3GA Sepharose®; or by hydrophobic interaction chromatography using such resins as phenyl ether, butyl ether, or propyl ether; or by immunoaffinity chromatography. Finally, one or more reverse-phase high performance liquid chromatography (RP-HPLC) steps employing hydrophobic RP-HPLC media, e.g., silica gel having pendant methyl or other aliphatic groups, can be employed to further purify the IL-113bc protein. Affinity columns including IL-13 or fragments thereof or including antibodies to the IL-13bc protein can also be used in purification in accordance with known methods. Some or all of the foregoing purification steps, in various combinations or with other known methods, can also be employed to provide a substantially purified isolated recombinant protein. Preferably, the isolated IL-13bc protein is purified so that it is substantially free of other mammalian proteins.

IL-13bc proteins of the invention may also be used to screen for agents which are capable of binding to IL-13bc or IL-13R or which interfere with the binding of IL-13 to the IL-13 or IL-13bc (either the extracellular or intracellular domains) and thus may act as inhibitors of normal binding and cytokine action ("IL-13R inhibitors"). Binding assays using a desired binding protein, immobilized or not, are well known in the art and may be used for this purpose using the IL-13bc protein of the invention. Purified cell based or protein based (cell free) screening assays may be used to identify such agents. For example, IL-13bc protein may be immobilized in purified form on a carrier and binding to purified IL-13bc protein may be measured in the presence and in the absence of potential inhibiting agents. A suitable binding assay may alternatively employ a soluble form of IL-13bc of the invention. Another example of a system in which inhibitors may be screened is described in Example 2 below.

In such a screening assay, a first binding mixture is formed by combining IL-13 or a fragment thereof and IL-13bc protein, and the amount of binding in the first binding mixture ($B_o$) is measured. A second binding mixture is also formed by combining IL-13 or a fragment thereof, IL-13bc protein, and the compound or agent to be screened, and the amount of binding in the second binding mixture (B) is measured. The amounts of binding in the first and second binding mixtures are compared, for example, by performing a calculation of the ratio $B/B_o$. A compound or agent is considered to be capable of inhibiting binding if a decrease in binding in the second binding mixture as compared to the first binding mixture is observed. Optionally, the second chain of IL-13R can be added to one or both of the binding mixtures. The formulation and optimization of binding mixtures is within the level of skill in the art, such binding mixtures may also contain buffers and salts necessary to enhance or to optimize binding, and additional control assays may be included in the screening assay of the invention.

Compounds found to reduce the binding activity of IL-13bc protein to IL-13 or its fragment to any degree, preferably by at least about 10%, more preferably greater than about 50% or more, may thus be identified and then secondarily screened in other binding assays and in vivo assays. By these means compounds having inhibitory activity for IL-13bc binding which may be suitable as therapeutic agents may be identified.

IL-13bc proteins, and polynucleotides encoding them, may also be used as diagnostic agents for detecting the expression or presence of IL-13bc, IL-13R, IL-13 or cells expressing IL-13bc, IL-13R or IL-13. The proteins or polynucleotides may be employed for such purpose in standard procedures for diagnostics assays using these types of materials. Suitable methods are well known to those skilled in the art.

As used herein "IL-13R" refers to IL-13bc and/or a second IL-13 receptor chain known as "IL-13Rα1" or "NR4" (see: murine receptor chain, Hilton et al., Proc. Natl. Acad. Sci. USA 1996, 93:497–501; human receptor chain, Aman et al., J. Biol. Chem. 1996, 271:29265–70, and Gauchat et al., Eur. J. Immunol. 1997, 27:971–8).

IL-13bc acts as a mediator of the known biological activities of IL-13. As a result, IL-13bc protein (particularly, soluble IL-13bc proteins), IL-13R inhibitors (i.e., antagonists of interaction of IL-13 with IL-13R (such as, for example, antibodies to IL-13R (including particularly to IL-13bc or to IL-13Rα1) and fragments thereof, antibodies to IL-13 and fragments thereof, soluble IL-13Rα1 proteins, and small molecule and other inhibitors of the interaction of IL-13 with IL-13R (including with IL-13bc and/or with IL-13Rα1)) may be useful in treatment or modulation of various medical conditions in which IL-13 is implicated or which are effected by the activity (or lack thereof) of IL-13 (collectively "IL-13-related conditions"). Mutated forms of IL-4 which bind to IL-13R can also be used as IL-13 antagonists (see, for example, those disclosed in Shanafelt et al., Proc. Natl. Acad. Sci. USA 1998, 95:9454–8; Aversa et al., J. Exp. Med. 1993, 178:2213–8; and Grunewald et al., J. Immunol. 1998, 160:4004–9).

IL-13-related conditions include without limitation Ig-mediated conditions and diseases, particularly IgE-mediated conditions (including without limitation atopy, allergic conditions, asthma, immune complex diseases (such as, for example, lupus, nephrotic syndrome, nephritis, glomerulonephritis, thyroiditis and Grave's disease)); inflammatory conditions of the lungs; immune deficiencies, specifically deficiencies in hematopoietic progenitor cells, or disorders relating thereto; cancer and other disease. Such pathological states may result from disease, exposure to radiation or drugs, and include, for example, leukopenia, bacterial and viral infections, anemia, B cell or T cell deficiencies such as immune cell or hematopoietic cell deficiency following a bone marrow transplantation. Since IL-13 inhibits macrophage activation, IL-13bc proteins may also be useful to enhance macrophage activation (i.e., in vaccination, treatment of mycobacterial or intracellular organisms, or parasitic infections).

IL-13bc proteins may also be used to potentiate the effects of IL-13 in vitro and in vivo. For example, an IL-13bc protein can be combined with a protein having IL-13 activity (preferably IL-13) and the resulting combination can be contacted with a cell expressing at least one chain of IL-13R other than IL-13bc (preferably all chains of IL-13R other than IL-13bc, such as IL-13Rα1). Preferably, the contacting step is performed by administering a therapeutically effective amount of such combination to a mammalian subject in vivo. The pre-established association of the IL-13 protein with the IL-13bc protein will aid in formation of the complete IL-13/IL-13R complex necessary for proper signaling. See for example the methods described by Economides et al., Science 270:1351 (1995).

IL-13bc protein and IL-13R inhibitors, purified from cells or recombinantly produced, may be used as a pharmaceutical composition when combined with a pharmaceutically acceptable carrier. Such a composition may contain, in addition to IL-13bc or inhibitor and carrier, various diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration.

The pharmaceutical composition of the invention may also contain cytokines, lymphokines, or other hematopoietic factors such as M-CSF, GM-CSF, interleukins (such as, IL-1, IL-2, IL-3, IL-4 . . . IL-24, IL-25), G-CSF, stem cell factor, and erythropoietin. The pharmaceutical composition may also include anti-cytokine antibodies. The pharmaceutical composition may further contain other anti-inflammatory agents. Such additional factors and/or agents may be included in the pharmaceutical composition to produce a synergistic effect with isolated IL-13bc protein or IL-13bc inhibitor, or to minimize side effects caused by the isolated IL-13bc or IL-13bc inhibitor. Conversely, isolated IL-13bc or IL-13bc inhibitor may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

The pharmaceutical composition of the invention may be in the form of a liposome in which isolated IL-13bc protein or IL-13bc inhibitor is combined, in addition to other pharmaceutically acceptable carriers, with amphipathic agents such as lipids which exist in aggregated form as micelles, insoluble monolayers, liquid crystals, or lamellar layers which in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, e.g., amelioration of symptoms of, healing of, or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of isolated IL-13bc protein or IL-13bc inhibitor is administered to a mammal. Isolated IL-13bc protein or IL-13bc inhibitor may be administered in accordance with the method of the invention either alone or in combination with other therapies such as treatments employing cytokines, lymphokines or other hematopoietic factors. When co-administered with one or more cytokines, lymphokines or other hematopoietic factors, IL-13bc protein or IL-13bc inhibitor may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering IL-13bc protein or IL-13bc inhibitor in combination with cytokine(s), lymphokine(s), other hematopoietic factor(s), thrombolytic or anti-thrombotic factors.

Administration of IL-13bc protein or IL-13bc inhibitor used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of IL-13bc protein or IL-13bc inhibitor is administered orally, IL-13bc protein or IL-13bc inhibitor will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% IL-13bc protein or IL-13bc inhibitor, and preferably from about 25 to 90% IL-113bc protein or IL-13bc inhibitor. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of IL-13bc protein or IL-13bc inhibitor, and preferably from about 1 to 50% IL-13bc protein or EL-13bc inhibitor.

When a therapeutically effective amount of IL-13bc protein or IL-13bc inhibitor is administered by intravenous, cutaneous or subcutaneous injection, IL-13bc protein or IL-13bc inhibitor will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to IL-13bc protein or IL-13bc inhibitor an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additive known to those of skill in the art.

The amount of IL-13bc protein or IL-13bc inhibitor in the pharmaceutical composition of the present invention will depend upon the nature and severity of the condition being treated, and on the nature of prior treatments which the patient has undergone. Ultimately, the attending physician will decide the amount of IL-13bc protein or IL-13bc inhibitor with which to treat each individual patient. Initially, the attending physician will administer low doses of IL-I 3bc protein or IL-13bc inhibitor and observe the patient's response. Larger doses of IL-13bc protein or IL-13bc inhibitor may be administered until the optimal therapeutic effect is obtained for the patient, and at that point the dosage is not generally increased further. It is contemplated that the various pharmaceutical compositions used to practice the method of the present invention should contain about 0.1 µg to about 100 mg (preferably about 20 µg to about 500 µg) of IL-13bc protein or IL-13bc inhibitor per kg body weight.

The duration of intravenous therapy using the pharmaceutical composition of the present invention will vary, depending on the severity of the disease being treated and the condition and potential idiosyncratic response of each individual patient. It is contemplated that the duration of each application of the IL-13bc protein or IL-13bc inhibitor will be in the range of 12 to 24 hours of continuous intravenous administration. Ultimately the attending physician will decide on the appropriate duration of intravenous therapy using the pharmaceutical composition of the present invention.

IL-13bc proteins of the invention may also be used to immunize animals to obtain polyclonal and monoclonal antibodies which specifically react with the IL-13bc protein and which may inhibit binding of IL-13 or fragments thereof to the receptor. Such antibodies may be obtained using the entire IL-13bc as an immunogen, or by using fragments of IL-13bc, such as the soluble mature IL-13bc. Smaller fragments of the IL-13bc may also be used to immunize animals. The peptide immunogens additionally may contain a cysteine residue at the carboxyl terminus, and are conjugated to a hapten such as keyhole limpet hemocyanin (KLH). Additional peptide immunogens may be generated by replacing tyrosine residues with sulfated tyrosine residues. Methods for synthesizing such peptides are known in the art, for example, as in R. P. Merrifield, J. Amer. Chem. Soc. 85, 2149–2154 (1963); J. L. Krstenansky, et al., FEBS lett. 211, 10 (1987).

Neutralizing or non-neutralizing antibodies (preferably monoclonal antibodies) binding to IL-13bc protein may also be useful therapeutics for certain tumors and also in the treatment of conditions described above. These neutralizing monoclonal antibodies may be capable of blocking IL-13 binding to the IL-13bc.

EXAMPLE 1

Isolation of IL-13bc cDNAs

Isolation of the Murine IL-13 Receptor Chain.

5 ug of polyA+ RNA was prepared from the thymuses of 6–8 week old C3H/HeJ mice. Double stranded, hemimethylated cDNA was prepared using Stratagene's cDNA synthesis kit according to manufacturers instructions. Briefly, the first strand was primed with an oligodT-Xho primer, and after second strand synthesis, EcORI adapters were added, and the cDNA was digested with XhoI, and purified. The cDNA was ligated to the XhoI-EcORI sites of the Zap Express (Stratagene) lambda vector, and packaged using Gigapak II Gold packaging extracts (Stratagene) according to the manufacturers instructions. A library of $1.5 \times 10^6$ resulting recombinant phage was amplified following manufacturer's instructions. This library was screened with a degenerate 17mer oligonucleotide probe of the sequence KSRCTCCABK CRCTCCA (SEQ ID NO:5) (K=G+T; S=C+G; R=A+G; B=C+G+T) using standard TMAC hybridization conditions as described (Current Protocols in Molecular Biology, Ausubel, et al., editors., John Wiley and Sons, 1995, section 6.4.3). Clone A25 was identified because it hybridized to the 17mer probe, but not to probes derived from known hematopoietin receptors. This clone was isolated in plasmid form from the ZapExpress vector as per manufacturers instruction, and the DNA sequence was determined. The DNA sequence encoded a novel member of the hematopoietin receptor family.

Clone A25 containing the polynucleotide having the sequence of SEQ ID NO:1 was deposited with ATCC as pA25pBKCMV at accession number 69997 on Feb. 22, 1996.

Isolation of the Human IL-13 Receptor Chain.

A partial fragment of the human homolog of the murine receptor was isolated by PCR using oligonucleotides derived from the murine sequence cDNA was prepared from human testis polyA+ RNA that was obtained from Clontech. A DNA fragment of 274 base pairs was amplified from this cDNA by PCR with the following oligonucleotides: ATAGTTAAAC-CATTGCCACC (SEQ ID NO:6) and CTCCATTCGCTC-CAAATTCC (SEQ ID NO:7) using AmpliTaq polymerase (Promega) in 1× Taq buffer containing 1.5 mM MgCl2 for 30 cycles of incubation (94° C.×1 minute, 42° C. for 1 minute, and 72° C. for 1 minute). The DNA sequence of this fragment was determined, and two oligonucleotides were prepared from an internal portion of this fragment with the following sequence: AGTCTATCTTACTTTTACTCG (SEQ ID NO:8) and CATCTGAGCAATAAATATTCAC (SEQ ID NO:9). These oligonucleotides were used as probes to screen a human testis cDNA library purchased from CLONTECH (cat #HL1161). Filters were hybridized at 52° C. using standard 5×SSC hybridization conditions and washed in 2×SSC at 52° C. Twenty two clones were isolated that hybridized to both oligonucleotides in a screen of 400,000 clones. DNA sequence was determined from four of the cDNA clones, and all encoded the same novel hematopoietin receptor. The predicted DNA sequence of the full length human receptor chain is shown as SEQ ID NO:3.

The human clone was deposited with ATCC as phA25#11pDR2 at accession number 69998 on Feb. 22, 1996.

EXAMPLE 2

Expression of Soluble IL-13bc Protein and Assay of Activity

Production and Purification of Soluble IL-13bc-Ig.

DNA encoding amino acids 1–331 of the extracellular domain of murine IL-13bc was fused to a spacer sequence encoding gly-ser-gly by PCR and ligated in frame with sequences encoding the hinge CH2 CH3 regions of human IgG1 of the COS-1 expression vector pED.Fc. IL-13bc-Ig was produced from DEAE-dextran transfected COS-1 cells and purified via protein A sepharose chromatography (Pharmacia).

B9 Proliferation Assay

Stimulation of proliferation of B9 cells (Aarden et al. Eur. J. Immunol. 1987. 17:1411–1416) in response to IL-13 or IL-4 was measured by 3H-thyrridine incorporation into DNA. Cells (5×103/well) were seeded into 96 well plates with media containing growth factors at varying concentrations in the presence or absence of IL-13bc-Ig at 1 ug/ml. After incubation for 3 days 1 uCi/well of 3H-thymidine was added and the cells incubated for an additional 4 hrs. Incorporated radioactivity was determined using a LKB 1205 Plate reader.

The B9 cell line proliferated in response to IL-13, IL-4 or IL-6. Only responses to L-13 were inhibited by the soluble IL-13bc-1 g, indicating that this receptor binds IL-13 specifically, but not IL-4 or IL-6. The tables show cpm. Two separate experiments are shown.

TABLE I

| cytokine dilution | IL-13 (3 ng/ml) | IL-13 plus A25-Fc (1 ug/ml) | IL-4 (20 ng/ml) | IL-4 plus A25-Fc (1 ug/ml) | Cos IL-6 (1/10,000) |
|---|---|---|---|---|---|
| 1 | 37734 | 1943 | 6443 | 6945 | 37887 |
| 1/3 | 30398 | 1571 | 2680 | 2442 | 36500 |
| 1/10 | 16101 | 1461 | 1767 | 1771 | 33335 |
| 1/30 | 2148 | 1567 | 1619 | 1783 | 27271 |
| 1/100 | 1574 | 1419 | 1522 | 1576 | 18831 |
| 1/300 | 1512 | 1531 | 1373 | 1577 | 7768 |
| 1/1000 | 1316 | 1392 | 1190 | 1474 | 2760 |
| 1/3000 | 1834 | 1994 | 1482 | 1819 | 1672 |

TABLE II

| cytokine dilution | IL-13 (3 ng/ml) | IL-13 plus A25-Fc (5 ug/ml) | IL-4 (20 ng/ml) | IL-4 plus A25-Fc (5 ug/ml) | Cos IL-6 (1/10,000) | Cos IL-6 plus A25-Fc (5 ug/ml) |
|---|---|---|---|---|---|---|
| 1 | 6413 | 295 | 1216 | 1158 | 6969 | 7703 |
| 1/3 | 5432 | 281 | 518 | 656 | 7827 | 8804 |
| 1/10 | 2051 | 281 | 489 | 520 | 8345 | 10027 |
| 1/30 | 506 | 319 | 279 | 476 | 8680 | 9114 |

TABLE II-continued

| cytokine dilution | IL-13 (3 ng/ml) | IL-13 plus A25-Fc (5 ug/ml) | IL-4 (20 ng/ml) | IL-4 plus A25-Fc (5 ug/ml) | Cos IL-6 (1/10,000) | Cos IL-6 plus A25-Fc (5 ug/ml) |
|---|---|---|---|---|---|---|
| 1/100 | 430 | 372 | 288 | 423 | 7426 | 10364 |
| 1/300 | 330 | 287 | 323 | 420 | 5531 | 6254 |
| 1/1000 | 326 | 389 | 348 | nt | 2524 | nt |
| no cytokine | 339 | 279 | 404 | 394 | 326 | 279 |

EXAMPLE 3

Direct Binding of Soluble IL-13bc to IL-13 Measured by Surface Plasmon Resonance (Biacore Analysis).

A Biacore biosensor was used to measure directly the specific binding of IL-13 to purified IL-13bc-Ig (Pharmacia, Johnsson et al., 1991). Approximately 10,000 to 17,000 resonance units (RU) of purified IL-13bc-Ig, human IgG1 or irrelevant receptor were each covalently immobilized to different flow cells on the sensor chip as recommended by the manufacturer. (RU's are a refelction of the mass of protein bound to the sensor chip surface.) Purified IL-13 was injected across the flow cells at 5 ul/min for 10 mins in the presence or absence of excess purified IL-13bc-1g. Binding was quantified as the difference in RU before and after sample injection. Specific IL-13 binding of 481.9 RU was observed only for immobilized IL-13bc-Ig whereas coinjection of IL-13 plus IL-13bc-Ig resulted in no binding to the immobilized IL-13bc-Ig (4 RU). No IL-13 binding was observed for either immobilized IgG or IL-11IR-Ig (5.4 and 3.7 RU respectively).

| Sample | IL-13bc-Ig (10,383 RU) | IgG control (13,399 RU) | IL-11R-Ig (17,182 RU) |
|---|---|---|---|
| 100 ng/ml human IL-13 | 481.9 RU bound | 5.4 RU bound | 3.7 RU bound |
| 100 ng/ml human IL-13 + soluble IL-13bc-Ig | 4.0 RU bound | not tested | not tested |

EXAMPLE 4

Binding of IL-13 Expressed in COS Cells to Labeled IL-13BC-Ig Fusion Protein: COS in situ Detection of IL-13 with IL-13bc–Fc Expression vectors for IL-13, IL4, IL-11 or empty vector were transfected into COS-1 cells in duplicated plates via the DEAE-dextran method. Two days after transfection cells were washed twice in phosphate buffered saline (PBS) and fixed in the culture dish for 10' at 4° C. with methanol. Following fixation cells were washed twice with PBS then rinsed once with binding buffer (PBS, 1% (w/v) bovine serum albumin,). 1% (w/v) sodium azide) and incubated for two hours at 4° C. in binding buffer with IL-13bc–fc at 10 ug/ml or with relevant anti-cytokine antisera. Cells were washed twice with PBS and incubated at 4° C. with shaking in alkaline phosphatase labeled Rabbit F(ab)2' anti-human IgG diluted 1:500 in binding buffer (for Fc fusion detection) or Rabbit F(ab)2' anti-rat IgG (for anti-cytokine detection). Cells were again washed twice in PBS. Alkaline phosphatase activity was visualized using nitro blue tetrazolium and 5-bromo-4-chloro-3-indolyl-phosphate.

Specific binding was visualized under the microscope. Only cells transfected with IL-13 showed specific binding to IL-13bc-Ig.

EXAMPLE 5

Other Systems for Determination Biological Activity of IL-13bc Protein

Other systems can be used to determine whether a specific IL-13bc protein exhibits a "biological activity" of IL-13bc as defined herein. The following are examples of such systems.

Assays for IL-13 Binding

The ability of a IL-13bc protein to bind IL-13 or a fragment thereof can be determine by any suitable assays which can detect such binding. Some suitable examples follow.

Binding of IL-13 to the extracellular region of the IL-13bc protein will specifically cause a rapid induction of phosphotyrosine on the receptor protein. Assays for ligand binding activity as measured by induction of phosphorylation are described below.

Alternatively, a IL-13bc protein (such as, for example, a soluble form of the extracellular domain) is produced and used to detect IL-13 binding. For example, a DNA construct is prepared in which the extracellular domain (truncated prior, preferably immediately prior, to the predicted transmembrane domain) is ligated in frame to a cDNA encoding the hinge $C_H2$ and $C_H3$ domains of a human immunoglobulin (Ig) γ1. This construct is generated in an appropriate expression vector for COS cells, such as pEDΔC or pMT2. The plasmid is transiently transfected into COS cells. The secreted IL-13bc-Ig fusion protein is collected in the conditioned medium and purified by protein A chromatography.

The purified IL-13bc-Ig fusion protein is used to demonstrate IL-13 binding in a number of applications. IL-13 can be coated onto the surface of an enzyme-linked immunosorbent assay (ELISA) plate, and then additional binding sites blocked with bovine serum albumin or casein using standard ELISA buffers. The IL-13bc-Ig fusion protein is then bound to the solid-phase IL-13, and binding is detected with a secondary goat anti-human Ig conjugated to horseradish peroxidase. The activity of specifically bound enzyme can be measured with a colorimetric substrate, such as tetramethyl benzidine and absorbance readings.

IL-13 may also be expressed on the surface of cells, for example by providing a transmembrane domain or glucosyl phosphatidyl inositol (GPI) linkage. Cells expressing the membrane bound IL-13 can be identified using the IL-13bc-Ig fusion protein. The soluble IL-13bc-Ig fusion is bound to the surface of these cells and detected with goat anti-human Ig conjugated to a fluorochrome, such as fluorescein isothiocyanate and flow cytometry.

Interaction Trap

A yeast genetic selection method, the "interaction trap" [Gyuris et al, Cell 75:791–803, 1993], can be used to determine whether a IL-13bc protein has a biological activity of IL-13bc as defined herein. In this system, the expression of reporter genes from both LexAop-Leu2 and LexAop-LacZ relies on the interaction between the bait protein, for example in this case a species which interacts with human IL-13bc, and the prey, for example in this case the human IL-13bc protein. Thus, one can measure the strength of the interaction by the level of Leu2 or LacZ expression. The most simple method is to measure the activity of the LacZ encoded protein, β-galactosidase. This activity can be judged by the degree of blueness on the X-Gal containing medium or filter. For the quantitative measurement of β-galactosidase activity, standard assays can be found in "Methods in Yeast Genetics" Cold Spring Harbor, N.Y., 1990 (by Rose, M. D., Winston, F., and Hieter, P.).

In such methods, if one wishes to determine whether the IL-13bc protein interacts with a particular species (such as, for example, a cytosolic protein which binds to the intracellular domain of the IL-13bc in vivo), that species can be used as the "bait" in the interaction trap with the IL-13bc protein to be tested serving as the "prey", or vice versa.

EXAMPLE 6

Inhibition of Fibrosis Using Soluble IL-13R

The development of fibrous tissue is part of the normal process of healing after injury. Nevertheless, in some circumstances there is a destructive accumulation of excess collagen that interferes with the normal function of the affected tissue. Indeed collagen synthesis and tissue scaring are the major pathological manifestations of a number of chronic and debilitating illnesses, including several autoimmune, allergic, and infectious diseases [1-7]. While there is a great deal of mechanistic information regarding the process of scar tissue formation [8,9], there are still large gaps in our understanding of the role of inflammatory cells and cytokines in initiating the fibrotic process.

As used herein "fibrosis" includes any condition which involves the formation of fibrous tissue (whether such formation is desireable or undesireable). Such conditions include, without limitation, fibrositis, formation of fibromas (fibromatosis), fibrogenesis (including pulmonary fibrogenesis), fibroelastosis (including endocardial fibroelastosis), formation of fibromyomas, fibrous ankylosis, formation of fibroids, formation of fibroadenomas, formation of fibromyxomas, and fibrocystotitis (including cystic fibrosis).

The IL-13 receptor complex is composed of at least three distinct components, including the IL4 receptor, the low-affinity binding IL-13Rα1 chain, and the high affinity binding chain, IL-13Rα2 [35,42-44]. Recently, a soluble IL-13Rα2-Fc fusion protein was prepared and has been used successfully to neutralize IL-13 both in vitro [35] and in vivo [30,39–41]. Since the fusion protein binds IL-13 with high affinity, but fails to neutralize IL-4, the protein provided an excellent tool to determine the specific roles of IL-13. In the present study, we used the IL-13 antagonist in wild type and IL-4-deficient mice in order to dissect the contributions of IL-13 and IL-4 to the development of hepatic fibrosis in murine schistosomiasis. In these studies, granuloma formation was examined in detail, focusing on eosinophil and mast cell recruitment and, more importantly, the development of egg-induced fibrosis was quantified using biochemical, histological, and molecular techniques. We also examined the contributions of IL-4 and IL-13 to the regulation of Th1/Th2-type cytokine responses both in vitro, in mesenteric lymph node cultures and, in vivo, in the granulomatous livers. While the results from this study show that IL-13 and IL4 exhibit some redundant activities in schistosomiasis pathogenesis, distinct functions for both cytokines were also clearly elucidated. Probably the most important and novel finding was the observation that IL-13, not IL4, was the major Th2-type cytokine driving type I and type III collagen mRNA production and hepatic fibrosis in infected mice. Thus, our findings establish that an IL-13 inhibitor/antagonist, such as IL-13Rα2-Fc, can be of therapeutic benefit in preventing fibrosis, such as, for example, that associated with chronic infectious disease.

Results

Comparative Effect of IL-4, IL-3 or Double IL-4/IL-13 Deficiencies in Schistosomiasis Pathogenesis: sIL-13Rα2-Fc Treatment Significantly Reduces Hepatic Fibrosis in *S. Mansoni*-Infected Mice To compare the regulatory roles of IL-4 and IL-13 in the pathogenesis of schistosomiasis, we infected C57BL/6 WT and IL-4 deficient mice percutaneously with 25 *S. mansoni* cercariae. Separate groups of animals were treated with either sIL-13Rα2-Fc or with control-Fc, as described in the Materials and Methods. The treatments began on week 5, at the start of egg laying, and all animals were sacrificed 8 wk postinfection and examined for several parasitologic and immunologic parameters. All four groups of mice harbored similar worm burdens, and tissue eggs produced per worm pair did not vary among the groups. At 8 wk postinfection, the time of the peak tissue response[45], WT mice showed no significant change in granuloma size as a result of IL-13 blockade. Interestingly, control-Fc treated IL-4 deficient mice also failed to show reduced granulomatous response, and in fact, granulomas were significantly larger in these mice. In striking contrast to these observations, the IL-4 deficient mice displayed a markedly reduced granulomatous response when IL-13 was inhibited. Indeed, the double IL-4 deficient/sIL-13Rα2-Fc-treated mice displayed on average a 40 to 50% reduction in granuloma volume when compared with either control or sIL-13Rα2-Fc-treated WT animals, and more than a 75% reduction when compared with control-Fc-treated IL-4 deficient mice.

The cellular composition of the lesions was also evaluated in Giesma-stained liver sections and IL-4 deficient mice displayed a marked reduction in granuloma-associated mast cells. In contrast, there was no change in mast cell numbers by IL-13 inhibition alone, and IL-13 bloackade had no additional effect on the already highly reduced numbers of mast cells in IL-4-deficient mice. Somewhat similar, yet distinct findings were observed when granuloma-associated eosinophils were evaluated. Here, the numbers of eosinophils were increased from 46 to 64% in WT mice by IL-13 blockade and significantly decreased (28%) as consequence of IL-4 deficiency. Despite the apparent contrasting roles for IL-13 and IL-4 in the tissue eosinophilia, an evenmore striking combined inhibitory effect was observed when the IL-4-deficient mice were treated with IL-13 inhibitor. In these mice, the average number of granuloma eosinophils was below 10%. Finally, there was no change in the degree of parenchymal or egg-asociated liver necrosis in the WT versus IL-4-deficient animals, while both sIL-13Rα2-Fc treated WT and IL-4 deficient groups showed marked reductions in overall parenchymal necrosis.

Perhaps most importantly, the sIL-13Rα2-Fc treatment alone significantly reduced the collage content of liver granulomas in WT mice, as assessed in tissue sections staind with picrosirius red. In contrast, infected IL-4-deficient mice showed no detectable change in granuloma collagen deposition by microscopic analysis. Interestingly, there appeared to be no combined or synergystic riole for IL-13 and IL-4 in this parameter since there was no significant difference between sIL-13Rα2-Fc-treated-WT and IL-4 deficient mice While similar worm numbers, tissue egg burdens, and granuloma sizes were found in control and sIL-13Rα2-Fc treated WT mice, IL-13 blockade had a substantial inhibitory effect on collagen deposition within the liver. Finally, the extent of hepatic fibrosis was also measured by the assessment of hydroxyproline levels, which is more quantitative than the histological techniques described above. The soluble IL-13 antagonist alone markedly decreased liver hydroxyproline levels, while the IL-4-deficiencyresulted in less significant reduction. The dual IL-4/IL-13 deficiency failed to reduce hydroxyproline to levels below that already observed in the sIL-13Rα2-Fc treated WT mice, although there was a slight trend in a second study (not significant). Together, these data demostrate that IL-13 is the dominant Th2-associated cytokine responsible for the development for the development of hepatic fibrosis in murine schistosomiasis.

Th2-Type Cytokine Production is Reduced in IL4-Deficient Mice but Unaffected by IL-13 Inhibition.

While it is well-Known that IL-4 is the primary cytokine driving CD4[+] Th2 cell development [21,22], the role of IL-13 in the generation and maintenance of Th2-type responses has been controversial and may be influenced by both host genetics and the infectious disease model under study [30,34,38]. Therefore, to determine whether the sIL-13Rα2-Fc-induced changes in liver pathology were generated by alterations in the Th1/Th2 cytokine balance, we isolated mesenteric lymph nodes and spleens from infected mice, prepared single cell suspensions, and restimulated the cultures in vitro with parasite antigens. Additional cell cultures were exposed to parasite antigens in the presence of anti-CD4 mAbs to determine whether cytokine production was dependent upon a CD4[+] T cell response. Culture supernatants were analyzed by ELISA for IL-4, IL-13, IL-5, IL-10, and IFN-γ. As might be predicted [15], mesenteric and splenic cultures (data not shown) prepared from WT mice displayed a highly polarized Th2-type cytokine response. They produce high levels of IL-4, IL-5, IL-10, and IL-13 in response to SEA stimulation and little or no IFN-γ. IL-4 deficient mice in constrast showed a more mixed Th1/Th2-type profile. Indeed, a significant SEA-specific IFN-γ response was detected in IL-4 deficient mice, which is consistent with previous studies [23,24]. IL-13, IL-10, and to a lesser extent IL-5, were also detected in these animals, although the levels of these cytokines were markedly decreased when compared with WT mice. Importantly, the maintenance of the low but significant IL-4-independent IL-13 response likely explains the marked granulomatous response that is maintained in the absence IL-4. Surprisingly, despite its marked inhibitory effect on hepatic fibrosis, sIL-13Rα2-Fc had no significant effect on Th1 or Th2-type cytokine responses in either WT or IL-4 deficient mice. It should also be noted that in all cases, cytokine production was highly dependent on a CD4[+] T cell response, since little or no cytokine expression was detected in any of the anti-CD4 mAb-treated SEA-stimulated cultures.

Changes in Th1/Th2-Type Cytokine mRNA Expression in the Granulomatous Livers of IL4-Deficient and sIL-3Rα2-Fc-Treated Mice.

To determine whether a similar pattern of cytokine expression was observed in vivo at the site of granuloma formation, we isolated liver mRNA from the various groups of mice at 8 wk postinfection and performed quantitative RT-PCR. Infected WT mice displayed a strong Th2-type cytokine mRNA profile, showing marked increases in IL-4, IL-13, IL-5, and IL-10 mRNA. The WT mice also showed modest increases in the expression of IFN-γ mRNA, which was consistent with previous observations [19]. In contrast to these findings, IL-13 and IL-5 mRNA levels were much lower in IL-4 deficient micem while IL-10 and TNF-α mRNA significantly increased and IFN-γ mRNA expression did not change. Again, similar to the in vitro results obtained from mesenteric lymph node and splenocyte cultures, IL-13 blockade had no significant effect on the pattern of cytokine mRNA expression in either WT or IL-4 deficient mice treated with the sIL-13Rα2-Fc, although this is unlikely to explain the decreases in fibrosis, since highly divergent levels of IL-10 were detected in sIL-13Rα2-Fc-treated WT versus IL-4 deficient mice, yet a similar decrease in fibrosis was observed. TGF-β1 and TGF-β2 mRNA expression was also examined in the granulomatous tissues, however no significant differences were observed in either infeced IL-4-deficient mice or in animals treated with sIL-13Rα2-Fc (data not shown).

Collagen I and Collagen III mRNA Levels are Reduced in the Livers of sIL-13Rα2-Fc-Treated Mice but Unaffected by IL-4-Deficiency.

The in vitro and in vivo cytokine studies decribed above suggested that the anti-fibrotic effect of sIL-13Rα2-Fc was unlikely to be explained by changes in Th1 or Th2-type cytokine expression. Therefore, in subsequent experiments, we investigated the patterns of collagen I (Col I) and collagen III (Col III) mRNA expression to determine whether the sIL-13Rα2-Fc-induced reduction in fibrosis was accompanied by direct changes in the expression of these two important collagen producing genes [19]. IL-13 blockade significantly reduced Col I and Col III mRNA expression in both WT and IL-4 deficient mice. There was no change in the infection-induced levels Col I or Col III mRNAs in IL-4-eficient mice and when compared with sIL-13Rα2-Fc-treated WT mice, there was no further reduction in similarly teated IL-4 deficient mice.

IL-13 Stimulates Collagen Production in Mouse 3T3Fibroblasts.

Having shown that IL-13 blockade in vivo significantly reduced Col I and Col III mRNA expression in the liver of infected WT and IL-4 deficient mice, we wanted to determine whether IL-13 would directly stimulate collagen synthesis in fibroblasts. To answer this question, we examined the induction of type I collagens in murine 3T3 fibroblasts by Western blotting. IL-13 induced collagen synthesis 48 h after stimulation. Minimal type I collagen was detected in unstimulated cells or at earlier time points in the cytokine-activated cultures (data not shown). IL-4 also induced collagen I synthesis and high levels of secreted collagen were easily detectable in the supernatants obtained from both cytokine-stimulated cultures (data not shown). The specificity of the reaction was confirmed by using purified collagen type I and bacterial collagenase treatments showed that the antibodies were specific for collagen (data not shown).

Discussion

A CD4+ Th2-type cytokine pattern dominates the immune response in mice infected with *S. mansoni* [12,13]. Previous IL-4 depletion studies and experiments with IL-4-deficient mice however, failed to show an indispensable role for this cytokine in the pathogenesis of schitosomiasis [15,23,24]. Indeed, while a partial reduction in fibrosis was observed in some studies [15], egg-induced granuloma formation could proceed in the complete absence of IL-4 [23,24]. In contrast to these observations, granuloma formation and the development of hepatic fibrosis was severely impaired in Stat6-deficient mice [16], which display a major defect in the production of several Th2-associated cytokines [46]. IL-4 and IL-13 both signal through Stat6, therefore the apparent differences in pathology observed between infected IL-4-deficient and Stat6-deficient mice may be explained by IL-13. Nevertheless, the distinct contributions of IL-4 and IL-13 in disease progression can not be discerned from studies in Stat6 or IL-4-deficient mice alone. In this study, we used a pot ent inhibitor of IL-13 in infected WT and IL-4-deficient mice and demonstrate that IL-13 and IL-4 exhibit redundant, as well as unique roles in the pathogenesis of schistosomiasis.

Several studies have shown that Th2-type cytokine responses can develop in vivo in the absence of IL-4 or the IL-4 receptor [26,39], which is consistent with our findings since reduced but significant IL-13, IL-10, and IL-5 expression was detectd in the mesenteric lymph nodes and livers of infected IL-4-deficient mice. Their production was also highly dependent on a CD4+ T cell response, further indicating that a conventional Th2-type response was established. These findings provide evidence that while maximal IL-13 expression is dependent on IL-4, the continued production of IL-13 might explain the maintenance of a significant granulomatous response in the absence of IL-4 [23-25]. Ideed, while blocking IL-13 alone had no effect on granuloma size in WT mice, inhibiting the residual IL-13 in IL-4-deficient mice resulted in a marked and highly significant reduction in granuloma volume. These findings demonstrate that IL-4 and IL-13 are both sufficient to mediate granuloma development, and formally explain the production of granulomas in IL-4-deficient mice versus the nearly complete lack of granulomas in Stat6-deficient mice [16,24]. They also support recent findings in the pulmonary egg granuloma model [30]. Because granulomas serve an important host-protective role by walling off potentially lethal hepatotxins released by the eggs [47], the host may have evolved redundant mechanisms for granuloma formation in order to ensure a favorable host-parasite relationship.

While these observations clearly demonstrate that IL-4 and IL-13 actively participate in granuloma formation, unique roles for both cytokines in mast cell recruitment, tissue eosinophilia, and most importantly, the generation of hepatic fibrosis were revealed in these studies. Histological examinations of liver sections from infected mice demonstrated that IL-13 is not required for mast cell or eosinophil differentiation and recruitment, since granulomas of sIL-13Rα2-Fc-treated WT mice showed no decrease in either cell type. In fact, eosinophil numbers were significantly increased in the lesions of IL-13-inhibited WT mice, suggesting that IL-13 may partially antagonize this effect. In contrast, mast cells were almost completely absent from the lesions in IL-4-deficient mice and eosinophils were decreased by over 50%. Interestingly, IL-13 appears to partially support the reduced but significant egg-induced tissue eosinophilia in IL-4-deficient mice since eosinophils were reduced to belo 10% in the IL-4-deficient/sIL-13Rα2-Fc-treated animals. Nevertheless, these data indicate that IL-4 is the dominant cytokine responsible for the development of eosinophil and mast cell populations within granulomas.

Probably the most important advance from this study was the finding that hepatic fibrosis could be blocked y sIL-13Rα2-Fc. Indeed, microscopic, biochemical, and molecular techniques all indicated that IL-13, not IL-4, plays the major role in the development of egg-induced liver fibrosis. Previous studies showed that the Th1/Th2 cytokine balance can significantly effect the extent of tissue fibrosis in *S. mansoni* infected mice [19]. Nevertheless, this study suggests that the effects of sIL-13Rα2-Fc were not mediated through a skewing of the Th cell cytokine response. Blocking IL-13 had no significant effect on the production of IFN-γ, IL-4, IL-5, IL-10, or IL-13 by mesenteric lymph node or spleen cells in vitro and there was also no change in cytokine mRNA expression in vivo, at the site of lesion formation. In contrast to these observations, IL-4-deficient mice displayed an increase IFN-γ response in the draining lymph nodes and decreased IL-5 and IL-13 expression in both the lymph nodes and live. Thus, the slight reduction in fibrosis detected in IL-4-deficient mice by hydroxyproline analysis may be attributable to decreased IL-13 production. The fact that IL-4 production was unaffected by IL-13 blockade, yet fibrosis was maximally reduced in these animals emphasizes the important role played by IL-13. Indeed, sIL-13Rα2-Fc-treated IL-4 deficient mice showed little additional decrease in hydroxyproline levels and no difference in Collagen I or III mRNA expression over that observed in similarly-treated WT mice. There was also no change in Collagen I or III expression in control-Fc-treated IL-4-deficinet mice when compared with WT anmials, further de-emphasizing the contribution of IL-4. Moreover, in vitro studies with 3T3 cells demonstreated for the first time the ability of UL-13 to stimulate collagen production in fibroblasts, thus the effects of IL-13 on fibrosis may be more direct and not dependent upon modulations in the Th1/Th2 cytokine response. In support of this conclusion, recent studies demonstrated that IL-13 receptors are expressed on fibroblasts [32] and that IL-13 increase adhesion molecule and inflammatory cytokine expression in human lung fibroblasts [48]. Finally, although IL-13 and IL-4[49] are both capable of promoting collage production in fibroblasts, the fact that cultured lymph node cells produced nearly 100-fold more IL-13 than IL-4, only serves to emphasize the potentially important contribution of IL-13 in this process. Indeed, studies in the pulmonary granuloma model revealed that IL-4 mRNA expression is more tightly regulated at the site of lesion formation, while the induction of IL-13mRNA is much more sustained over the [30]. Nevertheless, we have not examined the kinetics of IL-4 and IL-13 mRNA expression in infected animals, so we can not say whether a similar pattern holds in the granulomatous livers.

IL-13 was also recently shown to be important for resistance against intestinal nematodes [27,37-39]. Studies in IL-4 [39] and IL-13-deficient mice [37,38] suggested that IL-13, in contrast to IL-4, plays a requisite role in expulsion of both *N. brasiliensis* and *T. muris*. Nevertheless, the specific mechanism of worm expulsion remains unknown, although IL-4 and IL-13-induced changes in epithelial cells and gut physiology have been suggested as possible targets [50,51] IL-13 also plays a central role in murine asthma models. In these studies, IL-13 was found to be necessary and sufficient for the expression of allergic asthma [40,41]. Subepithelial fibrosis and airway smooth muscle hypertrophy are common features of chronic severe asthma [5] and chronic pulmonary fibrosis is associated with the production of type III and type I collagen in the early and late stages of the disease, respectively. Thus the link between IL-13 and fibrosis revealed in our study elucidates the etiology of several important human diseases and provides more effective modes of treatment of fibrotic diseases in general.

Our previous studies showed that an egg specific IL-12-induced Th1 memory response could effectively reduce hepatic fibrosis in subsequently-infected mice[19]. The reduction in pathology was accompanied by a switch in the normal Th2 response to one dominated by Th1-type cytokines. Findings from the current study suggest that the anti-pathology effects of this IL-12-based vaccination protocol may be explained by the inhibition of IL-13. Interestingly, a second study using a different protocol showed that repeated rIL-12 injections given at 6 to 8 weeks, during the Th2-dominated phase of granuloma development, was almost completely ineffective at blocking granuloma formation and fibrosis [52]. Related studies have suggested that IL-12 is less capable of modulating established Th2-type responses[53], which likely explains the failure to modulate pathology in the latter study [52] In contrast to these findings, sIL-13Rα2-Fc was extremely effective at reducing hepatic fibrosis, even though administered only during the later stages of infection. These findings indicate that IL-13 antagonism is a much more effective therapeutic approach to reduce fibrosis in situations where pathogenic Th2-type immune responses have already been established. In summary, our findings provide evidence that IL-13 inhibitors, such as the sIL-13Rα2-Fc, are of general therapeutic benefit in preventing fibrosis associated with chronic infectious disease and demonstrate the important and non-redundant role of IL-13 in the pathogenesis of schistosomiasis.

Methods

Animals, Parasites and Ag Preparations

6–8 week old female C57BL/6 and IL-4-deficient mice (C57BL/6 background, $10^{th}$ backcross) were obtained from Taconic Farms, Inc. (Germantown, N.Y.). All mice were housed in a NIH American Association for the Accreditation of Laboratory Animal Care-approved animal facility in sterile filter-top cages and maintained on sterile water. Cercariae of a Puerto Rican strain of Schistosoma mansoni (NMRI) were obtained from infected Biomphalaria glabrata snails (Biomedical Research Institute, Rockville, Md.). Soluble egg antigen (SEA) was purified from homogenized eggs, as previously described [15].

Reagents

The soluble IL-13 receptor α2-Fc fusion protein (sIL-13Rα2-Fc) was prepared as previously described [35] and provided by Genetics Institute, Cambridge Mass. Endotoxin contamination was <2 EU/mg, as determined with the Cape Cod Associates LAL assay (Limulus Amebocyte Lysate, Woods Hole, Mass.). The in vitro ID50, as determined by the ability to neutralize 3ng/ml of murine IL-13 in the B9 proliferation assay, was approximately 10 ng/ml. Human IgG (control-Fc), which was used as a control for sIL-13Rα2-Fc, was affinity purified by recombinant Protein A-Sepharose chromatography, as described for sIL-13Rα2-Fc 35. As described previously, the control-Fc had no detectable effect on pathology or cytokine expression in infected mice [30].

Infection and Treatments

Mice were infected by percutaneous challenge of tail skin for 40 min in water containing between 20 and 25 cercariae. Animals were treated with either a human control-Fc or with the sIL-13Rα2-Fc by i.p. injection in 0.5 ml PBS, every other day after the onset of egg production (week 5). The optimal concentration for in vivo use (200 µg/mouse/day) was chosen based on kinetic assays and on dose response experiments in sensitized/i.v. egg-injected mice [30]. Sera were collected from mice on the day of sacrifice. All animals were sacrificed by i.p. administration of sodium pentobarbital (18 mg/mouse, Sigma, St. Louis, Mo.) on week 8 and perfused with citrated saline to assess worm burdens [15]. No mortality was observed among any of the treated groups.

Histopathology and Fibrosis Measurement

For measurement of granulomas, approximately half of the liver was fixed with Bouin-Hollande fixative and processed as previously described [15]. The size of hepatic granulomas was determined in histological sections stained by Wright's Giemsa stain (Histopath of America, Clinton, Md.). The diameters of each granuloma containing a single viable egg were measured with an ocular micrometer and the volume of each granuloma calculated assuming a spherical shape. The mean of the longest diameter and the diameter perpendicular to that was used. The percentage of eosinophils, mast cells and other cell types were evaluated in the same sections. Parenchymal necrosis was scored on a scale of 0–4, with 0 being the least and 4 being the most extensive necrosis. The frequency of mast cells was also assigned on a similar scale, using a range from 0–4. The number of schistosome eggs in the liver and gut and the collagen content of the liver, determined as hydroxyproline, were measured as described previously [15]. Fibrosis was also scored histologically using sections stained with picrosirius red. The picrosirius reagent stains collagen specifically and when sections are viewed under polarizing light, the bright areas where collagen is deposited are illuminated. All granulomas within each section were scored for picrosirius (red) "density" based on a scale 1–4, and a second measurement of "area involved" was also determined using the same scale. The total fibrosis score was determined by multiplying the density and area for each granuloma (ie. a score of 16 would be the maximum). An average of 30 granulomas per mouse was included in all analyses. To control for consistency, the same individual scored all histological features and had no knowledge of the experimental design.

Isolation and Purification of RNA

Two portions of the liver from each animal were combined and placed in 1 ml of RNA-STAT 60 (Tel-Test), frozen on dry ice and kept at −70° C. until use. Tissues were homogenized using a tissue polytron (Omni International Inc., Waterbury, Conn.) and total RNA was extracted following the recommendations of the manufacturer. The RNA was resuspended in DEPC-treated water and quantitated spectrophotometrically.

RT-PCR Detection of Cytokine mRNA

A RT-PCR procedure was used to determine relative quantities of mRNA for IL-4, IL-5, IL-10, IL-13, IFN-γ, collagen I, collagen III, TGFβ1, TGFβ2, and HPRT (hypoxanthine-guanine phosphoribosyl transferase). The cDNA was obtained after reverse transcription of 1 µg of RNA as described [14]. The primers and probes for all genes were previously published [14,19,54]. The PCR cycles used for each cytokine were as follows: IL-4 (33), IL-5 (31), IFN-γ (29), collagen I (26), collagen III (22), TGFβ1 (34), TGFβ2 (34), and HPRT (23).

Analysis and Quantification of PCR Products

The amplified DNA was analyzed by electrophoresis, Southern blotting and hybridization with non-radioactive cytokine-specific probes as previously described [14]. The PCR products were detected using a ECL detection system (Amersham). The chemiluminescent signals were quantified using a flat-bed scanner (Microtek model 600 ZS, Torrance, Calif.). The amount of PCR product was determined by comparing the ratio of cytokine-specific signal density to that of HPRT-specific signal density for individual samples. Arbitrary densitometric units for individual samples were subsequently multiplied by a factor of 100.

In Vitro Cultures

Mesenteric lymph node (MLN) cells and spleens were extracted from the mice and single cell suspensions were prepared. Red blood cells were lysed by osmotic treatment with ACK lysing buffer (Biofluids, Inc., Rockville, Md.). Cells were placed in RPMI 1640 medium supplemented with 10% FCS, 2 mM glutamine, 100 U/ml penicillin, 100 μg/ml streptomycin, 25 mM HEPES, 1 mM sodium pyruvate, 0.1 mM nonessential amino acids, and 50 μM 2-ME at 37° C. in 5% $CO_2$. Cells were plated in 24-well plates ($3 \times 10^6$/ml, 1 ml) and stimulated with SEA (20 μg/ml) and supernatants were collected after 72 h to measure the levels of IL-4, IL-5, IL-10, IL-13 and IFN-γ. Additional SEA-stimulated cultures were also treated with 50 μg/ml of anti-CD4 mAb (GK1.5). Cultures treated with anti-CD4 mAb alone showed no change in cytokine expression when compared with that observed in medium control cultures (data not shown). IL-5, IL-10, and IFN-γ were measured using specific sandwich ELISA [15]. IL-13 levels were measured using murine IL-13 ELISA kits (R&D Systems, Minneapolis, Minn.). Cytokine levels were calculated from curves prepared with recombinant cytokines. IL-4 was measured using the IL-4 sensitive cell line CT.4S. Proliferation of these cells was quantified by ($^3$H)TdR incorporation, and the amount of cytokine was determined by comparison with known amounts of recombinant IL-4.

Western Blot Detection of Collagen I

3T3 fibroblasts were cultured in RPMI 1640 medium supplemented with 10% FCS, 2 mM glutamine, 100 U/ml penicillin, 100 μg/ml streptomycin, 25 mM HEPES, 1 mM sodium pyruvate, 0.1 mM nonessential amino acids, and 50 μM 2-ME at 37° C. in 5% $CO_2$. Confluent cells were plated in 24-well plates (500,000 cells/ml) and stimulated with IL-4 (1000 U/ml) or rIL-13 (R&D Systems, Minneapolis, Minn.) (20 μg/ml) for 6, 24 and 48 hs. Culture supernatants were collected to analyze secreted collagen I. Cells were washed once with phosphate buffered saline and lysed with SDS-PAGE sample buffer. Cell lysates and culture supernatants were submitted to electrophoretic separation in 6% tris-glycine gels (Novel Experimental Technology, San Diego, Calif.) using reducing conditions, and transferred to nitrocellulose membranes (Schleicher & Schuell, Keene, N.H.). Blots were probed with rabbit IgG anti-mouse type I collagen (Biodesign International, Kennenbunk, Me.) and peroxidase labelled anti-rabbit IgG (Amersham Pharmacia Biotech, Inc., Piscataway,N.J.) was used as a second Ab. The bands were visualized using a western blot chemiluminescence reagent (NEN Life Science Products, Boston, Mass.). To confirm identity of the collagen bands, cell lysates were treated with 0.5 mg/ml of collagenase (Boehringer Mannheim, Indianapolis, Ind.) in PBS, supplemented with 1 mM $CaCl_2$ and 1% FCS, for 1 h at 37° C. A purified rat collagen I preparation was also used as a control.

Statistics

Schistosome worm and egg numbers, changes in cytokine mRNA, and values for secreted cytokine proteins were compared using Student's two-tailed t test. Hepatic fibrosis was compared by analysis of covariance, using the log of total liver eggs as the covariate and the log of hydroxyproline per egg. $p < 0.05$ was considered significant.

REFERENCES

1. Rosenstein, B. J. & Zeitlin, P. L. Cystic fibrosis. *Lancet* 351, 277–282 (1998).
2. Lee, J. K. et al. A serine elastase inhibitor reduces inflammation and fibrosis and preserves cardiac function after experimentally-induced murine myocarditis. *Nat Med* 4, 1383–1391 (1998).
3. Lahita, R. G. Collagen disease: the enemy within. *Int J Fertil Womens Med* 43,229–234 (1998).
4. Kuroda, K., Tsukifuji, R. & Shinkai, H. Increased expression of heat-shock protein 47 is associated with overproduction of type I procollagen in systemic sclerosis skin fibroblasts. *J Invest Dermatol* 111, 1023–1028 (1998).
5. Bento, A. M. & Hershenson, M. B. Airway remodeling: potential contributions of subepithelial fibrosis and airway smooth muscle hypertrophy/hyperplasia to airway narrowing in asthma. *Allergy Asthma Proc* 19, 353–358 (1998).
6. Wahl, S. M. et al. Bacterial cell wall-induced hepatic granulomas. An in vivo model of T cell-dependent fibrosis. *J Exp Med* 163, 884–902 (1986).
7. Henderson, G. S. et al. Two distinct pathological syndromes in male CBA/J inbred mice with chronic *Schistosoma mansoni* infections. *Am J Pathol* 142, 703–714 (1993).
8. Trojanowska, M., LeRoy, E. C., Eckes, B. & Krieg, T. Pathogenesis of fibrosis: type 1 collagen and the skin. *J Mol Med* 76, 266–274 (1998).
9. Johnson, L. L., Dyer, R. & Hupe, D. J. Matrix metalloproteinases. *Curr Opin Chem Biol* 2, 466–471 (1998).
10. Cheever, A. W. & Yap, G. S. Immunologic basis of disease and disease regulation in schistosomiasis. *Chem Immunol* 66, 159–176 (1997).
11. Bergquist, N. R. Schistosomiasis vaccine development: progress and prospects [In Process Citation]. *Mem Inst Oswaldo Cruz* 93, 95–101 (1998).
12. Grzych, J. M. et al. Egg deposition is the major stimulus for the production of Th2 cytokines in murine schistosomiasis mansoni. *J. Immunol.* 146, 1322–1327 (1991).
13. Pearce, E. J., Caspar, P., Grzych, J. M., Lewis, F. A. & Sher, A. Downregulation of Th1 cytokine production accompanies induction of Th2 responses by a parasitic helminth, *Schistosoma mansoni. J. Exp. Med.* 173, 159–162 (1992).
14. Wynn, T. A. et al. Analysis of cytokine mRNA expression during primary granuloma formation induced by eggs of *Schistosoma mansoni. J. Immunol.* 151, 1430–1440 (1993).
15. Cheever, A. W. et al. Anti-IL-4 treatment of *Schistosoma mansoni*-infected mice inhibits development of T cells and non-B, non-T cells expressing Th2 cytokines while decreasing egg-induced hepatic fibrosis. *J. Immunol.* 153, 753–754 (1994).
16. Kaplan, M. H., Whitfield, J. R., Boros, D. L. & Grusby, M. J. Th2 cells are required for the *Schistosoma mansoni* egg-induced granulomatous response. *J Immunol* 160, 1850–1856 (1998).
17. Chensue, S. W. et al. Role of interleukin-4 and gamma-interferon in *Schistosoma mansoni* egg-induced hypersensitivity granuloma formation: orchestration, relative contribution and relationship to macrophage function. *J. Immunol.* 148, 900–910 (1992).
18. Henderson, G. S., Lu, X., McCurley, T. L. & Colley, D. G. In vivo molecular analysis of lymphokines involved in the murine immune response during *Schistosoma mansoni* infection: II. Quantitation of IL-4 mRNA, EFN-g mRNA, and IL-2 mRNA levels in the granulomatous livers, mesenteric lymph nodes, and spleens during the course of modulation. *J. Immunol.* 148, 2261–2267 (1992).

19. Wynn, T. A. et al. An IL-12-based vaccination method for preventing fibrosis induced by schistosome infection. *Nature* 376, 594–596 (1995).

20. Secor, W. E., Stewart, S. J. & Colley, D. G. Eosinophils and immune mechanisms. VI. The synergistic combination of granulocyte-macrophage colony-stimulating factor and IL-5 accounts for eosinophil-stimulation promoter activity in *Schistosoma mansoni*-infected mice. *J Immunol* 144, 1484–1489 (1990).

21. Le Gros, G., Ben-Sasson, S. Z., Seder, R., Finkelman, F. D. & Paul, W. E. Generation of interleukin 4 (IL-4)-producing cells in vivo and in vitro: IL-2 and IL-4 are required for in vitro generation of IL-4-producing cells. *J Exp Med* 172, 921–929 (1990).

22. Kopf, M. et al Disruption of the murine IL-4 gene blocks Th2 cytokine responses. *Nature* 362, 245–248 (1993).

23. Metwali, A. et al. The granulomatous response in murine Schistosomiasis mansoni does not switch to Th1 in IL4-deficient C57BU6 mice. *J Immunol* 157, 4546–4553 (1996).

24. Pearce, E. J. et al. *Schistosoma mansoni* in IL-4-deficient mice. *Int Immunol* 8, 435–444 (1996).

25. Chensue, S. W., Warmington, K., Ruth, J. H., Lukacs, N. & Kunkel, S. L. Mycobacterial and schistosomal antigen-elicited granuloma formation in IFN-gamma and IL-4 knockout mice: analysis of local and regional cytokine and chemokine networks. *J Immunol* 159, 3565–3573 (1997).

26. Noben-Trauth, N. et al. An interleukin 4 (IL-4)-independent pathway for CD4+ T cell IL-4 production is revealed in IL-4 receptor-deficient mice. *Proc Natl Acad Sci USA* 94, 10838–10843 (1997).

27. Barner, M., Mohrs, M., Brombacher, F. & Kopf, M. Differences between IL-4R alpha-deficient and IL-4-deficient mice reveal a role for IL-13 in the regulation of Th2 responses. *Curr Biol* 8, 669–672 (1998).

28. Amiri, P. et al. Tumour necrosis factor alpha restores granulomas and induces parasite egg-laying in schistosome-infected SCID mice. *Nature* 356, 604–607 (1992).

29. Hernandez, H. J., Wang, Y. & Stadecker, M. J. In infection with *Schistosoma mansoni*, B cells are required for T helper type 2 cell responses but not for granuloma formation. *J Immunol* 158, 4832–4837 (1997).

30. Chiaramonte, M. G. et al. IL-13 is a key regulatory cytokine for Th2 cell-mediated pulmonary granuloma formation and IgE responses induced by *Schistosoma mansoni* eggs. *J Immunol* 162, 920–930 (1999).

31. de Vries, J. E. The role of IL-13 and its receptor in allergy and inflammatory responses. *J Allergy Clin Immunol* 102, 165–169 (1998).

32. Murata, T., Husain, S. R., Mohri, H. & Puri, R. K. Two different IL-13 receptor chains are expressed in normal human skin fibroblasts, and IL-4 and IL-13 mediate signal transduction through a common pathway. *Int Immunol* 10, 1103–1110 (1998).

33. Emson, C. L., Bell, S. E., Jones, A., Wisden, W. & McKenzie, A. N. Interleukin (IL)-4-independent induction of immunoglobulin (Ig)E, and perturbation of T cell development in transgenic mice expressing IL-13. *J Exp Med* 188, 399–404 (1998).

34. McKenzie, G. J. et al. Impaired development of Th2 cells in IL-13-deficient mice. *Immunity* 9, 423–432 (1998).

35. Donaldson, D. D. et al. The Murine IL-13Rα2: Molecular Cloning, Characterization and Comparison with Murine IL-13Ra1. *J. Immunol.* 161, 2317–24. (1998).

36. Minty, A. et al. Interleukin-13 is a new human lymphokine regulating inflammatory and immune responses. *Nature* 362, 248–250 (1993).

37. McKenzie, G. J., Bancroft, A., Grencis, R. K. & McKenzie, A. N. A distinct role for interleukin-13 in Th2-cell-mediated immune responses. *Curr Biol* 8, 339–342 (1998).

38. Bancroft, A. J., McKenzie, A. N. & Grencis, R. K. A critical role for IL-13 in resistance to intestinal nematode infection. *J Immunol* 160, 3453–3461 (1998).

39. Urban, J. F., Jr. et al. IL-13, IL4Ralpha, and Stat6 are required for the expulsion of the gastrointestinal nematode parasite *Nippostrongylus brasiliensis*. *Immunity* 8, 255–264 (1998).

40. Wills-Karp, M. et al. Interleukin-13: central mediator of allergic asthma. *Science* 282, 2258–2261 (1998).

41. Grunig, G. et al. Requirement for IL-13 independently of IL4 in experimental asthma. *Science* 282, 2261–2263 (1998).

42. Hilton, D. J. et al. Cloning and characterization of a binding subunit of the interleukin 13 receptor that is also a component of the interleukin 4 receptor. *Proc Natl Acad Sci USA* 93, 497–501 (1996).

43. Miloux, B. et al. Cloning of the human IL-13R alpha1 chain and reconstitution with the IL4R alpha of a functional IL4/IL-13 receptor complex. *FEBS Lett* 401, 163–166 (1997).

44. Gauchat, J. F. et al. A novel 4-kb interleukin-13 receptor alpha mRNA expressed in human B, T, and endothelial cells encoding an alternate type-II interleukin-4/interleukin-13 receptor. *Eur J Immunol* 27, 971–978 (1997).

45. Warren, K. S. Schistosomiasis: host-pathogen biology. *Rev Infect Dis* 4, 771–775 (1982).

46. Kaplan, M. H., Schindler, U., Smiley, S. T. & Grusby, M. J. Stat6 is required for mediating responses to IL-4 and for development of Th2 cells. *Immunity* 4, 313–319 (1996).

47. Dunne, D. W., Jones, F. M. & Doenhoff, M. J. The purification, characterization, serological activity and hepatotoxic properties of two cationic glycoproteins (alpha 1 and omega 1) from *Schistosoma mansoni* eggs. *Parasitology* 103 Pt 2, 225–236 (1991).

48. Doucet, C. et al. IL-4 and IL-13 specifically increase adhesion molecule and inflammatory cytokine expression in human lung fibroblasts. *Int Immunol* 10, 1421–1433 (1998).

49. Serpier, H. et al. Antagonistic effects of interferon-gamma and interleukin-4 on fibroblast cultures. *J Invest Dermatol* 109, 158–162 (1997).

50. Zund, G., Madara, J. L., Dzus, A. L., Awtrey, C. S. & Colgan, S. P. Interleukin-4 and interleukin-13 differentially regulate epithelial chloride secretion. *J Biol Chem* 271, 7460–7464 (1996).

51. Finkelman, F. D. et al. Cytokine regulation of host defense against parasitic gastrointestinal nematodes: lessons from studies with rodent models. *Annu Rev Immunol* 15, 505–533 (1997).

52. Boros, D. L. & Whitfield, J. R. Enhanced Th1 and dampened Th2 responses synergize To inhibit acute granulomatous and fibrotic responses in murine schistosomiasis mansoni [In Process Citation]. *Infect Immun* 67, 1187–1193 (1999).

53. Wang, Z. E. et al. Interferon gamma-independent effects of interleukin 12 administered during acute or established infection due to *Leishmania major. Proc Natl Acad Sci USA* 91, 12932–12936 (1994).

54. Wynn, T. A., Eltoum, I., Oswald, I. P., Cheever, A. W. & Sher, A. Endogenous interleukin 12 (IL-12) regulates granuloma formation induced by eggs of *Schistosoma mansoni* and exogenous IL-12 both inhibits and prophylactically immunizes against egg pathology. *J. Exp. Med.* 179, 1551–1561 (1994).

and literature references cited herein are incorporated by reference as if fully set forth.

---

What is claimed is:

1. A method of treating tissue fibrosis in a mammalian subject, said method comprising administering to said subject a therapeutically effective amount of a composition comprising (a) an antibody to IL-13 or an IL-13 binding fragment of an antibody to IL-13; and (b) a pharmaceutically acceptable carrier, thereby treating tissue fibrosis in said subject.

2. The method of claim 1, wherein tissue fibrosis affects a tissue selected from the group consisting of liver, skin epidermis, skin endodermis, muscle, tendon, cartilage, cardiac tissue, pancreatic tissue, lung tissue, uterine tissue, neural tissue, testis, ovary, adrenal gland, artery vein, colon, small intestine biliary tract and gut.

3. The method of claim 2 wherein said tissue is liver.

4. The method of claim 3 wherein said fibrosis is that resulting from infection with schistosoma.

5. The method of claim 1 wherein said fibrosis is that resulting from healing of a wound.

6. The method of claim 1 wherein said wound is a surgical incision.

7. The method of claim 1, wherein said composition comprises an antibody to IL13.

8. The method of claim 1, wherein said composition comprises an IL-13 binding fragment of an antibody to IL-13.

9. The method of claim 1, wherein said antibody antagonizes binding of IL-13 to a human IL-13bc.

10. The method of claim 7, wherein said antibody antagonizes binding of IL-13 to a human IL-13bc.

11. The method of claim 8, wherein said antibody antagonizes binding of IL-13 to a human IL-13bc.

12. The method of claim 1, wherein said composition is administered by intravenous, cutaneous, subcutaneous, or intravenous injection.

13. The method of claim 1, wherein said composition is administered by intravenous injection.

14. The method of claim 10, wherein said antibody is administered for about 12 to 24 hours of continuous administration.

15. The method of claim 1, wherein said composition is administered at a dose of about 0.1 µg to about 100 mg per kg body weight.

16. The method of claim 1, wherein said composition is administered at a dose of about 20 µg to about 500 µg per kg body weight.

17. The method of claim 1, wherein said antibody is a monoclonal antibody.

18. A method of inhibiting formation of tissue fibrosis in a mammalian subject, said method comprising administering to said subject a therapeutically effective amount of a composition comprising (a) an antibody to IL-13 or an IL-13 binding fragment of and IL-13 antibody; and (b) a pharmaceutically acceptable carrier, thereby inhibiting formation of tissue fibrosis in said subject.

19. The method of claim 18 wherein tissue fibrosis affects a tissue selected from the group consisting of liver, skin epidermis, skin endodermis, muscle, tendon, cartilage, cardiac tissue, pancreatic tissue, lung tissue, uterine tissue, neural tissue, testis, ovary, adrenal gland, artery vein, colon, small intestine biliary tract and gut.

20. The method of claim 18 wherein said tissue is liver.

21. The method of claim 20 wherein said fibrosis is that resulting from infection with schistosoma.

22. The method of claim 18 wherein said fibrosis is that resulting from healing of a wound.

23. The method of claim 22 wherein said wound is a surgical incision.

24. The method of claim 18, wherein said composition comprises an antibody to IL-13.

25. The method of claim 18, wherein said composition comprises an IL-13 binding fragment of an antibody to IL-13.

26. The method of claim 18, wherein said antibody antagonizes binding of IL-13 to a human IL-13bc.

27. The method of claim 24, wherein said antibody antagonizes binding of IL-13 to a human IL-13bc.

28. The method of claim 25, wherein said antibody antagonizes binding of IL-13 to a human IL-13bc.

29. The method of claim 18, wherein said composition is administered by intravenous, cutaneous, subcutaneous, or intravenous injection.

30. The method of claim 18, wherein said composition is administered by intravenous injection.

31. The method of claim 30, wherein said antibody is administered for about 12 to 24 hours of continuous administration.

32. The method of claim 24, wherein said composition is administered at a dose of about 0.1 µg to about 100 mg per kg body weight.

33. The method of claim 24, wherein said composition is administered at a dose of about 20 µg to about 500 µg per kg body weight.

34. The method of claim 18, wherein said antibody is a monoclonal antibody.

* * * * *